US011806311B2

(12) United States Patent
Schobel et al.

(10) Patent No.: US 11,806,311 B2
(45) Date of Patent: Nov. 7, 2023

(54) SYSTEM AND METHOD FOR MAKING PERSONALIZED INDIVIDUAL UNIT DOSES CONTAINING PHARMACEUTICAL ACTIVES

(71) Applicant: Aquestive Therapeutics, Inc., Warren, NJ (US)

(72) Inventors: Alexander Mark Schobel, Warren, NJ (US); Keith Kendall, Warren, NJ (US); Dan Barber, Warren, NJ (US); Theresa Wood, Warren, NJ (US); Peter Boyd, Warren, NJ (US); John Maxwell, Warren, NJ (US)

(73) Assignee: Aquestive Therapeutics, Inc., Warren, NJ (US)

( * ) Notice: Subject to any disclaimer, the term of this patent is extended or adjusted under 35 U.S.C. 154(b) by 665 days.

(21) Appl. No.: 16/447,107

(22) Filed: Jun. 20, 2019

(65) Prior Publication Data

US 2019/0388302 A1    Dec. 26, 2019

Related U.S. Application Data

(60) Provisional application No. 62/688,107, filed on Jun. 21, 2018, provisional application No. 62/700,444, (Continued)

(51) Int. Cl.
*A61J 3/00* (2006.01)
*G16H 20/17* (2018.01)
*G16H 20/13* (2018.01)

(52) U.S. Cl.
CPC .............. *A61J 3/00* (2013.01); *G16H 20/13* (2018.01); *G16H 20/17* (2018.01); (Continued)

(58) Field of Classification Search
CPC ...... A61J 3/00; A61J 2200/70; A61J 2205/10; G16H 20/13; G16H 20/17
See application file for complete search history.

(56) References Cited

U.S. PATENT DOCUMENTS 9,400,933 B2   7/2016 Jaynes
2008/0300718 A1   12/2008 Austin et al.
(Continued)

FOREIGN PATENT DOCUMENTS

CN    103250176 A    8/2013
WO    2012/021899 A2    2/2012

OTHER PUBLICATIONS

Anonymous, "Arzt per App—Telemedizin auf dem Prüfstand (Archive)" (English Title: "Doctor via app—Telemedicine put to the test"), May 7, 2018, https://www.deutschlandfunk.de/arzt-pe r-app-telemedizin-auf-dem-pruefstand.724.d.html?dram:article id=417347.
(Continued)

*Primary Examiner* — Reginald R Reyes
(74) *Attorney, Agent, or Firm* — Hoffmann & Baron, LLP

(57) ABSTRACT

Systems and methods for making and delivering personalized, medically prescribed pharmaceuticals to an individual patient are described. Individual unit doses (IUDs) of medicine may be prepared specific to the individual in need of same, by using a system, which includes a networked control system in combination with manufacturing assemblies specific to the IUDs and delivering the medicine to the patient directly from the manufacturer.

20 Claims, 5 Drawing Sheets

Related U.S. Application Data filed on Jul. 19, 2018, provisional application No. 62/729,051, filed on Sep. 10, 2018.

(52) U.S. Cl.
CPC ........ *A61J 2200/70* (2013.01); *A61J 2205/10* (2013.01); *A61J 2205/20* (2013.01)

(56) References Cited

U.S. PATENT DOCUMENTS

| 2011/0224502 | A1 | 9/2011 | Herbst | |
|---|---|---|---|---|
| 2013/0204430 | A1* | 8/2013 | Davey | G06F 30/13 |
| | | | | 700/216 |
| 2013/0325496 | A1* | 12/2013 | Nasso | G16H 20/10 |
| | | | | 705/2 |
| 2018/0075558 | A1* | 3/2018 | Hill, Sr. | G16H 70/40 |
| 2018/0369248 | A1* | 12/2018 | Niichel | A23P 10/35 |
| 2019/0134200 | A1* | 5/2019 | Lubda | A61K 31/496 |
| 2020/0246272 | A1* | 8/2020 | Beck | A61K 9/4808 |
| 2020/0306198 | A1* | 10/2020 | Beck | A61K 9/4816 |

OTHER PUBLICATIONS

Baehr, Michael, et al., "How to introduce dose dispensing at hospitals, including integration and the closed loop medication administration?", Jun. 30, 2015, Hamburg, Germany, https://www.lakemedelsakademin.se/wp-c ontent/uploads/2015/06/MichaelBaehr.pdf.

Anonymous, "Arzt per App—Telemedizin auf dem Prüfstand (Archive)", May 7, 2018, https://www.deutschlandfunk.de/arzt-per-app-telemedizin-auf-dem-pruefstand.724.d.html?dram:article id=417347.

* cited by examiner

SYSTEM AND METHOD FOR MAKING PERSONALIZED INDIVIDUAL UNIT DOSES CONTAINING PHARMACEUTICAL ACTIVES

CROSS-REFERENCE TO RELATED APPLICATION

This application claims priority to U.S. Provisional Patent Application No. 62/688,107 filed on Jun. 21, 2018, U.S. Provisional Patent Application No. 62/700,444 filed on Jul. 19, 2018, and U.S. Provisional Patent Application No. 62/729,051 filed on Sep. 10, 2018, the contents of which are incorporated herein by reference in its entirety.

BACKGROUND

Field

The present disclosure relates to systems and methods of making personalized individual unit doses (IUDs) for delivering a prescribed amount of active to an individual. In particular, the present disclosure relates to methods of tailoring the manufacture of IUDs in accordance with an individual's prescription for a particular active and delivering the manufactured IUD to the patient.

Related Art

Currently, IUDs are available in various forms, including tablets, caplets, capsules, wafers, films, sheets, injectable pens, creams, ointments, gels and syringes, among others. The IUDs are typically made by pharmaceutical manufacturers and contain dosages of an active or actives in accordance with the government-approved amounts and for government-approved indications. Conventionally, an individual patient (human or other animal) is assessed by a medical professional and given a prescription for a particular treatment protocol. The prescription is limited to the dosage amounts, which are government approved and hence commercially available. The patient proffers the prescription to a licensed prescription filler, such as a pharmacy, which carries an inventory of IUDs purchased from manufacturers. The prescription filler fulfills the prescription for the individual patient. In some cases, the prescription is communicated directly to the prescription filler from the medical professional. In other instances, the IUDs are mailed to the patient from the prescription filler.

Currently, prescriptions are fulfilled in compliance with the government-approved dosage amounts, which in most cases is sufficient for patients, but is not always the amount the medical professional believes is proper for the patient, such as with off-label uses. For example, a medical professional may inform a patient to cut the IUD in half so that only half (or some other portion) of the active is consumed at any one time. Alternatively, the medical professional may instruct the patient to take a larger dosage than the approved amount for the particular treatment. In some cases the medical professional may prescribe a particular active and dose for a different medical indication than for which the active is approved. Such off-label use and variation in dose is currently done on a patient-by-patient basis, but what is lacking in the current method of fulfilling prescriptions is the customization (personalization) of the specific IUD to a specific individual, as well as a more efficient and cost-effective way of producing IUDs personalized to the medical needs of an individual patient. Also, currently, pharmacies are primarily dispensers of IUDs, although some pharmacies are licensed compounders, and are thus permitted to provide certain compounding (combining of ingredients including the active) of medications, particularly when two or more drugs (actives) are to be incorporated into a prescription. In general, compounding is a practice in which a licensed pharmacist, a licensed physician, or, in the case of an outsourcing facility, a person under the supervision of a licensed pharmacist, combines, mixes, or alters ingredients of a drug to create a medication tailored to the needs of an individual patient. Compounding by pharmacists has obvious limitations because of lack of manufacturing equipment, process knowledge, quality control, manufacturing facilities and know-how. Sometimes, the health needs of a patient cannot be met by an FDA-approved medication, for example, if a patient has an allergy and needs a medication to be made without a certain component, e.g., dye; or if an elderly patient or a child can't swallow a pill and needs a medicine in a liquid form that is not otherwise available. Moreover, compounded drugs are not FDA-approved. This means that FDA does not verify the safety, or effectiveness of compounded drugs. Consumers and health professionals rely on the drug approval process to ensure that drugs are safe and effective and made in accordance with Federal quality standards. Compounded drugs also lack an FDA finding of manufacturing quality before such drugs are marketed.

There is a need for a system of making to-order personalized IUDs, which is efficient, less costly, and which maintains the good manufacturing and quality control standards currently required by governmental agencies. There is also a need for a system and method for making to-order personalized IUDs, which reduce or alleviate inventory, thus further reducing overhead and the costs associated therewith.

SUMMARY

A system is disclosed for creating one or more personalized individual unit doses (IUDs) comprising a prescribed amount of active for treatment of an individual. The system comprising: an apparatus for making the personalized IUD, and a networked system configured to electronically communicate health information measured from the individual. The apparatus is used to make the IUD in accordance with the medical prescription and is selected from the group consisting of a film forming assembly, a capsule-filling assembly, a tablet-forming assembly, a tablet-coating assembly, a blending (mixing) assembly, a powder-forming assembly, a granulating assembly, a spray-drying assembly, an extruder assembly, a compounding assembly, a packaging assembly, a labeling assembly, an embossing assembly, a scoring assembly, a quality control assembly and combinations thereof. The health information is electronically communicated to a medical professional who determines a medical prescription that includes a prescribed amount of active in the personalized IUD. The networked system may include a processor, memory storage and executable instructions; and at least one of a display device, an alpha-numeric input device, a cursor control device, a drive unit, a machine-readable medium, and a signal generation device. The system may also include a biometric measurement module that interfaces with the individual. The biometric measurement module may include an invasive device and/or non-invasive measurement device, or a combination thereof.

In another aspect of this disclosure, there is provided a method of producing a personalized IUD containing an active for an individual. That method includes: a) obtaining biometric measurements relating to the health of the individual; b) transmitting the biometric measurements to a manufacturer of medical or prescription products; c) manufacturing the IUD in accordance with a medical prescription specific to the individual; and d) delivering the IUD made in accordance with the medical prescription to the individual. The method may further include the step of electronically transmitting the biometric measurements of the individual to a medical professional authorized to write the medical prescription, and/or electronically transmitting the medical prescription to the manufacturer, prior to the step of manufacturing the IUD. Manufacturing the IUD may comprise using an apparatus and/or adding the active to a carrier matrix. Manufacturing the IUD may include the step of forming the IUD in one or more individual wells, and/or adding the active to an already formed IUD. The IUD may be film, wafer, capsule, tablet, suspension, solution, ointment, patch, cream, gel, troche, ampule, vial, syrup, tincture, spirit, lozenge, balm, liniment, injection or any combination thereof. When it is a film, it may be single-layered or multi-layered. The active may be in a first film layer, a second film layer or both. The active may be selected from the group consisting of: small molecules, macromolecules, biologics, microorganisms, allergens, enzymes, and combinations thereof.

Another aspect is a method for creating one or more personalized individual unit doses (IUDs) containing a prescribed amount of active for distribution and administration to an individual. The method comprises the steps of: (a) providing a medical professional with personal health information of the individual; (b) prescribing by the medical professional, a medical prescription comprising an amount of active to be administered to the individual as determined, at least in part, on the personal health information, the medical prescription comprising a treatment regimen for administering a prescribed amount of the active per personalized individual unit dose (IUD); (c) electronically communicating at least a part of the medical prescription to a manufacturer of IUDs; (c) manufacturing the IUD using an apparatus for making personalized IUDs; and (d) distributing the IUDs to the individual.

Embodiments of the disclosed subject matter will become apparent from the following detailed description, which is to be read in connection with the accompanying drawings.

BRIEF DESCRIPTION OF THE DRAWINGS

The following drawings are presented by way of example only and without limitation, wherein like reference numerals, when used, indicate corresponding elements throughout the several views, and wherein.

It is to be appreciated that elements in the figures are illustrated for simplicity and clarity. Common but well-understood elements that are useful in a commercially feasible embodiment are not necessarily shown in order to facilitate a less hindered view of the illustrated embodiments.

DETAILED DESCRIPTION

The present disclosure provides a system and method of manufacturing personalized IUDs by using a network-enabled control system to measure, communicate, produce and deliver IUDs specific to a prescription provided to an individual. Thus, the individual, e.g. a patient, may telecommunicate with a medical professional and measure, using medical devices, the biometrics as directed by the physician, various biometrics to allow the medical professional to diagnose a condition, treatment, regimen and/or medical prescription. The medical prescription is then communicated to a manufacturing facility, where the specific dosage forms and dosage amounts, i.e. IUDs, are made in accordance with the prescribed active, dosage form and dosage amount per IUD.

Thus in one aspect of this disclosure, there is provided a method of producing personalized IUDs directly from the manufacturer, meaning that the manufacturer is provided with the patient prescription information and fulfills the prescription by manufacturing the IUDs according to the specification of the prescription. The IUDs are personalized to the individual and made to order. Thus the manufacturer IUDs may then be shipped to the pharmacy, medical professional, distributor or directly to the patient. Communication(s) between the medical professional, IUD manufacturer and individual patient may provide for modifications to the prescription and hence modifications in the manufacturing of the IUDs, as well as renewals to existing prescriptions and IUD manufacturing.

The system and method of manufacturing personalized IUDs disclosed herein solves the problems in the art described above. Accordingly to this disclosure, personalized IUDs may be sent directly to a patient from a manufacturer (or distributor of the manufacturer), thereby improving efficiency and costs, as well as appropriating other benefits.

Furthermore, the present disclosure allows for the tracking of a patients prescription fulfillment history, whereby the manufacturer can directly communicate via the network-enabled control system with the patient and/or the medical professional for continued treatment, either the same or modified treatment.

Figure 1:
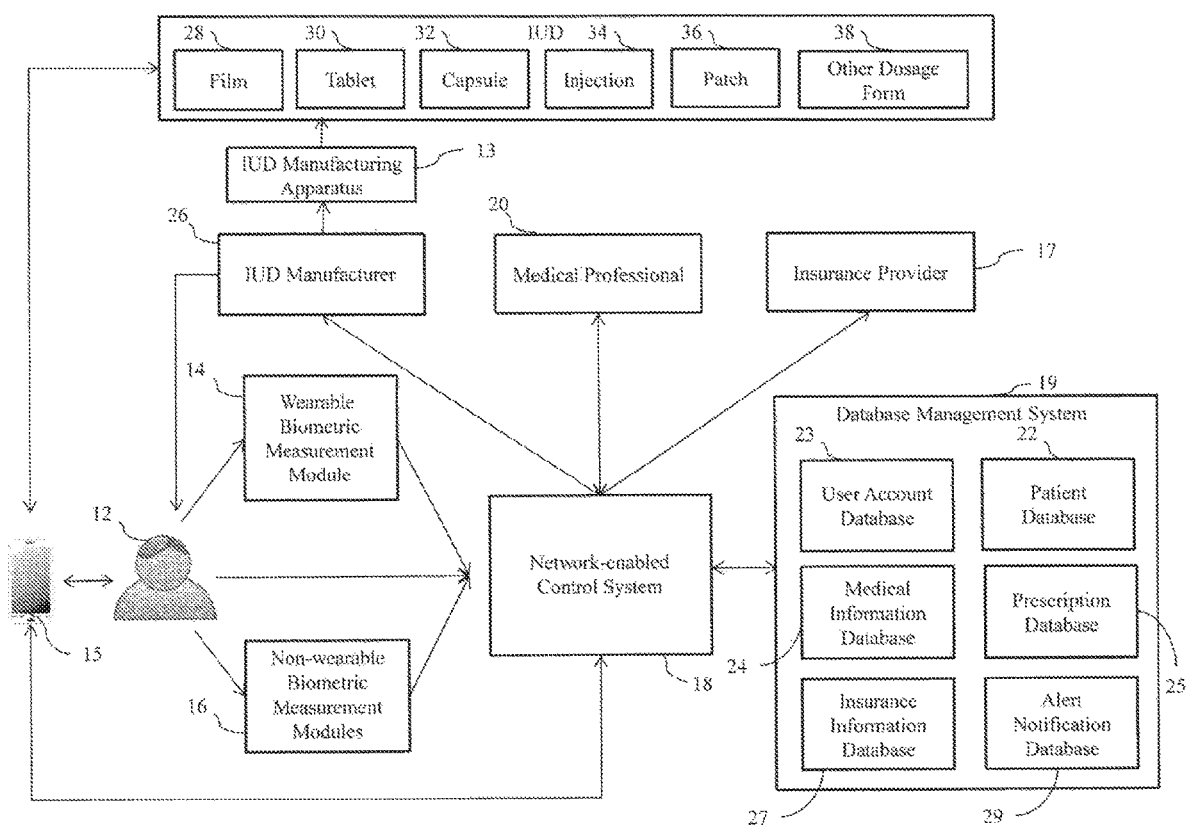
FIG. 1 is a block diagram of a system for making personalized individual unit doses (IUDs) to deliver a prescribed amount of active to an individual.

FIG. 1 shows a block diagram of a system 10 for making personalized individual unit doses (IUDs) to deliver a prescribed amount of active to an individual 12. The system 10 according to the present invention generally includes an apparatus 13 operated by an IUD manufacturer 26 for making the personalized IUDs, a network-enabled control system 18 configured to electronically communicate health information measured from the individual 12, and optionally a biometric measurement module 14, 16 that interfaces with the individual 12.

Figure 3:
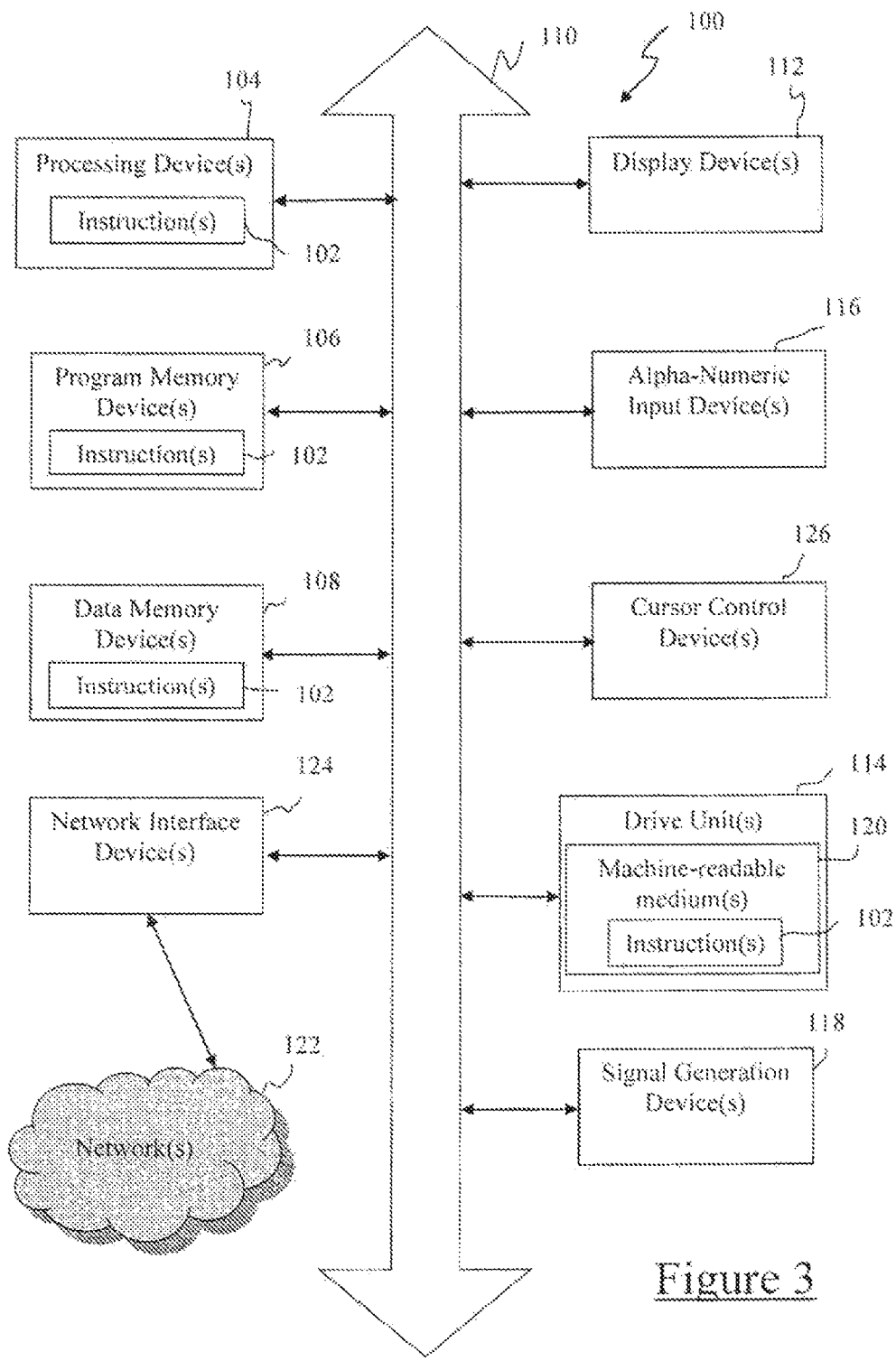
FIG. 3 is a block diagram showing at least a portion of an exemplary machine in the form of a computing system configured to perform certain methods disclosed herein.

Biometric information is measured, obtained, and/or collected from the individual 12 using a wearable biometric measurement module 14 and/or a non-wearable biometric measurement module 16. Alternatively, biometric information may be directly entered into the computer by the individual 12, or the medical professional 20 may receive the biometric information visually through the network, e.g., the medical professional 20 may observe the patient via the network-enabled control system 18. The biometric information is thus provided to the network-enabled control system 18 for processing and distribution. The processed biometric information is then provided to a medical professional 20. The medical professional 20, optionally has access to a patient database 22 and/or a medical information database 24. The network-enabled control system 18 has access to the patient database 22 so that patient-specific information can be utilized during processing of the biometric information. Further detail regarding the network-enabled control system 18 is shown in FIG. 3, which provides a block diagram of one embodiment of the network-enabled control system 18.

Once the biometric information of the individual 12 is collected and processed, the medical professional 20 may provide a prescription to the IUD manufacturer 26 based on information obtained from the network-enabled control system 18, patient database 22, and/or medical information database 24, as well as the processed biometric information. Using the network-enabled control system 18, the IUD manufacturer 26 uses the prescription obtained from the medical professional 20 to manufacture the IUDs, which can be in any form, non-limiting examples of which include a film 28, tablet 30, capsule 32, injection 34, patch 36, and/or other dosage form 38. The film 28, tablet 30, capsule 32, injection 34, patch 36, and/or other dosage form 38 are then provided to the user 12, desirably in appropriate packaging and desirably labelled appropriately with the active name, e.g., drug name, as well as the dose, i.e., the amount of drug present in the IUD, commonly referred to as the "labelled amount", and instructions for use, e.g., how often the dose is to be taken, with or without food, precautions to be taken or other important/useful instructions.

For packaging and delivery of IUDs, the IUD manufacturer 26 may separately package each manufactured IUD for the individual 12 or may co-pack (package together) a plurality of IUDs that are manufactured based on one or more prescriptions specific to the individual 12. The co-packing method may consolidate all medications that the individual 12 is prescribed during a given period of time, thus, providing an easy and convenient delivery and compliance option for the individual 12, who may be required to take one or more medications at different time intervals, e.g., morning, evening, daily, weekly, biweekly, bimonthly, and combinations thereof. Co-packing may include separate packaging units with IUDs, which may be more than one type of drug, for each day or for a designated dosage protocol. For example, the patient 12 may be required to take two medications concurrently, but at different frequencies, i.e., one medication daily and the other medication weekly. In order to assist the individual 12 to correctly follow the medication instructions and properly comply with prescription protocol, each manufactured IUD may include indicia, such as a color-code, on its packaging which contains the medication instructions. For example, a daily IUD's pouch may be red-colored whereas a weekly IUD's pouch may be blue-colored.

Alternatively, a scannable code technology, such as a QR code, may be implemented to provide appropriate medication information and instructions for each packaged IUD, or for each IUD per se (i.e., the code is printed or embossed on the IUD itself). The QR code may store any encrypted or non-encrypted information or data related to the individual 12, manufactured IUDs, and medication instructions, such as individual's name, IUD manufacturer, drug name, labelled amount, frequency of medication (e.g., once daily, twice daily, once weekly, etc.), when-to-take information (e.g., before or after meal), dosage, etc. This QR code (not shown) may be printed on each pouch of the manufactured IUDs, or on the IUDs themselves, before delivery and can be scanned by the mobile device 15 of the individual 12 to direct the mobile device 15 to easily and conveniently display information stored in the QR code to the mobile device 15. The mobile device 15 is installed with an application program capable of scanning and recognizing two dimensional barcodes of the QR code. The QR code allows the individual 12 to repeatedly retrieve the medication information and instructions of the IUD as long as the QR code is not damaged.

Figure 2:
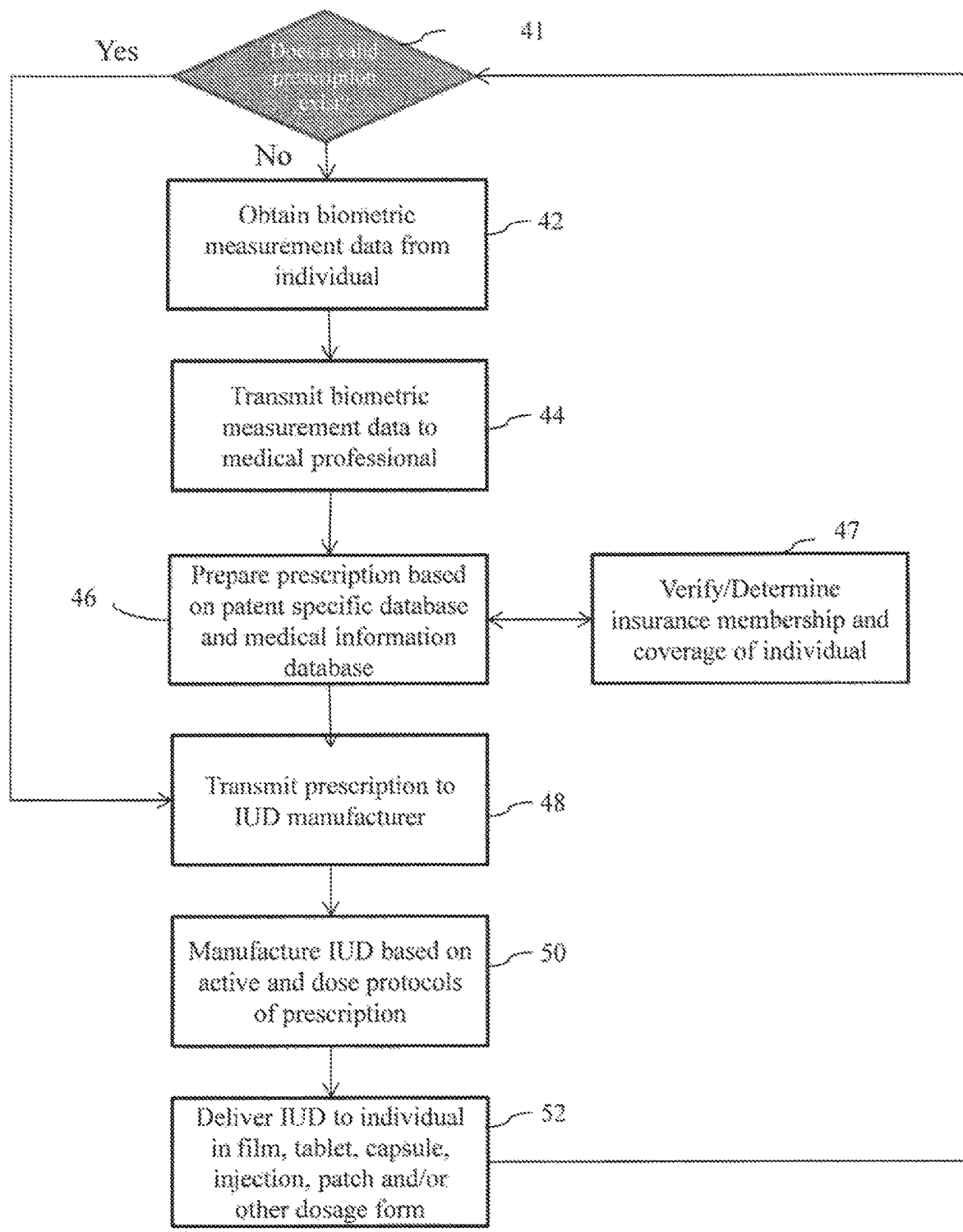
FIG. 2 is a flowchart of a method for making personalized IUDs to deliver a prescribed amount of an active to an individual.

FIG. 2 shows a flow chart of a method of making personalized IUDs to deliver a prescribed amount of active to an individual 12. A determination of whether a valid prescription is made in step 41. If a valid prescription does not exist, biometric measurement data is obtained from the individual in step 42, and transmitted to the medical professional 20 in step 44 using, for example, the wearable and/or non-wearable biometric measurement module 14, 16 and network-enabled control system 18. The biometric measurement data may alternatively be input by the individual 12 and/or observed by the medical professional 20. The prescription may be prepared by the medical professional 20 based on the biometric information in step 46, and optionally based on information obtained from the patient database 22, and/or medical information database 24. Then, in step 47, insurance membership and coverage (e.g., copayment, deductible, etc.) of the individual 12 may be verified and determined by an insurance provider 17. In addition to the verification of the individual's 12 insurance membership/status, the step 47 allows the insurance provider 17 to process bills and/or claims once the prescription is prepare by the medical professional 20. The prescription may be then transmitted, desirably electronically, to the IUD manufacturer 26 in step 48. The IUD is manufactured via the IUD manufacturing apparatus 13 based on active and dose protocols in the prescription in step 50, and delivered to the individual in film 28, tablet 30, capsule 32, injectable form 34, patch 36, and/or other dosage form 38 in step 52. If a valid prescription does exist as determined in step 41, the process proceeds to step 48. Following step 52, the process returns to step 41 to again determine whether there is a valid prescription.

Figure 4:
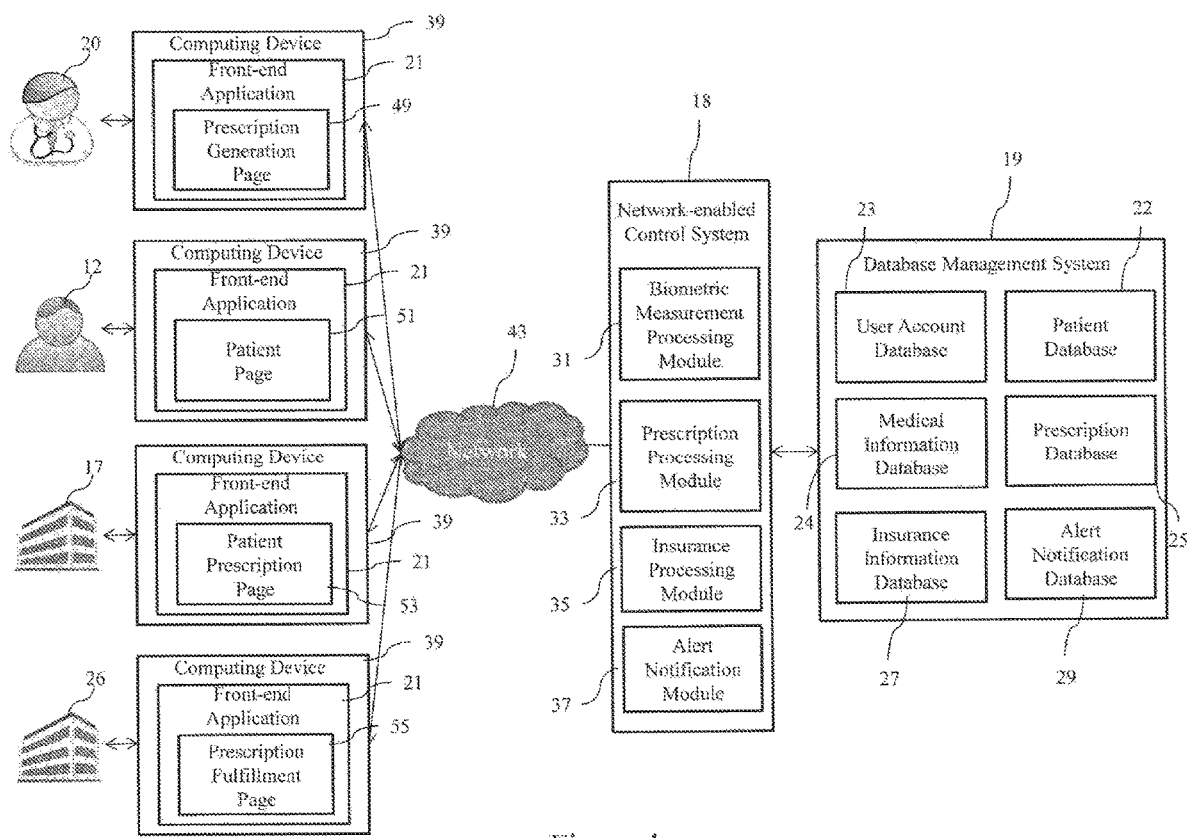
FIG. 4 is a block diagram of a prescription fulfillment system for electronically creating a prescription and filling the prescription by manufacturing personalized IUDs according to the specification of the prescription.

In another embodiment of the present invention, FIG. 4 shows a prescription fulfillment system 11 capable of collecting, analyzing, and processing information and data to assist in electronically creating a prescription and filling the prescription by manufacturing personalized IUDs according to the specification of the prescription.

The present embodiment is described below with reference to flowchart illustrations and/or block diagrams of methods, apparatuses (systems), and computer program products according to the embodiment. It will be understood that each block of the flowchart illustrations and/or block diagrams, and combinations of blocks in the flowchart illustrations and/or block diagrams, may be implemented by computer program instructions.

Providing such computer program instructions to the "server," "device," "computing device," "general purpose computer," "computer device," "system," or "specialized computing device" causes a machine to produce executable programs, such that when executed, they create means for implementing the functions/acts specified in the flowchart and/or block diagram block or blocks. These computer program instructions may also be stored in a computer-readable medium that may direct a computing device or other programmable data processing apparatus to function in a particular manner, such that the instructions stored in the computer-readable medium produce an article of manufacture including instruction means which implement the function/act specified in the flowchart and/or block diagram block or blocks.

The present embodiment is not necessarily limited to any particular number, type or configuration of processors, nor to any particular programming language, memory storage format or memory storage medium.

As used herein, a "participant" refers to a patient 12, medical professional 20, insurance provider 17, or IUD manufacturer 26. A "patient" refers generally to a prescription recipient; a "medical professional" refers generally to a treating physician or other medical professional who is authorized to issue a prescription to a plurality of patients; an "insurance provider" refers generally to an insurance benefit plan provider; and an "IUD manufacturer" refers generally to a prescription drug manufacturer/provider.

The prescription fulfillment system 11 is designed and configured such that each participant (patient 12, medical professional 20, insurance provider 17, and IUD manufacturer 26) involved in the process of writing a prescription, authorizing insurance coverage, and manufacturing personalized IUDs according to the present invention may access and utilize the prescription fulfillment system 11 to perform necessary tasks for completing the process for electronically creating a prescription and filling the prescription by manufacturing personalized IUDs according to the specification of the prescription.

The prescription fulfillment system 11 leverages both the biometric measurement information data obtained and collected from the patient 12 and various medical and health related information stored in the medical information database 24 to allow the medical professional 20 to electronically formulate and process prescriptions and thereby, allowing the IUD manufacturer 26 to precisely produce the personalized IUDs based on the specification of the prescription.

The prescription fulfillment system 11 provides several benefits to the patient 12. More particularly, the prescription fulfillment system 11 provides the patient 12 with easy and convenient ways to view and manage patient's prescriptions and medications by providing a comprehensive list of patient's medications, a comprehensive list of patient's prescriptions, information related to each medication, information related to each prescription, medication instructions, delivery status of manufactured IUDs, etc. The prescription fulfillment system 11 also provides IUDs which are made and tailored (personalized) specifically for the individual patient in accordance with the prescription and delivered to the patient 12. In addition to the time and convenience aspects of the process and system 11 described in this disclosure, the personalized IUDs may be manufactured to ensure a higher level of patient safety because they are made taking into account a patient's medical history.

The prescription fulfillment system 11 provides benefits to the medical professional 20 as well. More particularly, the prescription fulfillment system 11 provides an easy and convenient way for the medical professional 20 to formulate and prescribe prescriptions by utilizing a plurality of modules configured in the network-enabled control system 18 and the comprehensive information stored in a plurality of databases. In addition, the prescription fulfillment system 11 acts as a central repository where all the electronic prescriptions are saved and stored such that the medical professional 20 may easily retrieve prescriptions or any particular prescription. Each of the plurality of modules and each of the plurality of databases will be discussed in greater detail below.

Referring again to FIG. 4, the prescription fulfillment system 11 generally includes a network-enabled control system 18, a database management system 19 operatively linked to the network-enabled control system 18, a front-end application 21, and optionally a biometric measurement module 14, 16 that interfaces with the patient 12 and is operatively linked to the network-enabled control system 18. The database management system 19 is configured to manage a plurality of databases, including, but not limited to, a user account database 23, a patient database 22, a medical information database 24, a prescription database 25, an insurance information database 27, and an alert notification database 29. While in the depicted embodiment in FIG. 4 shows one database management system 19, the prescription fulfillment system 11 may be designed and configured to include more than one database management system. Thus, alternately, each of the plurality of databases 22, 23, 24, 25, 27, 29 may be separately managed by individual database management system 19.

As shown in FIGS. 3 and 4, the network-enabled control system 18 includes one or more processing devices 104 or computing processing units (CPUs) 104. The one or more CPUs 104 may include application-specific circuitry including the operative capability to execute the prescribed operations integrated therein, for example, an application specific integrated circuit (ASIC) and/or microprocessor. The one or more CPUs 104 are configured to interface with the plurality of databases 22, 23, 24, 25, 27, 29 in the database management system 19. The CPUs 104 are operative to act on a program or set of instructions stored in the database management system 19. Execution of the program or set of instructions configured in the database management system 19 causes one of the CPUs 104 to carry out tasks such as locating data, retrieving data, processing data, etc. In addition, the one or more CPUs 104 can execute the plurality of modules (biometric measurement processing module 31, prescription processing module 33, insurance processing module 35, and alert notification processing module 37) configured in the network-enabled control system 18, The plurality of modules 31, 33, 35, 37 may be executed to collect, analyze, and process information to assist in creating a prescription and filling the prescription by manufacturing IUDs according to the specification of the prescription.

The user account database 23 may be configured to store information associated with the participants 12, 17, 20, 26 of the prescription fulfillment system 11. As stated above, the participants of the prescription fulfillment system 11 are all parties involved in prescribing and filling the prescriptions such as patients 12, medical professionals 20, insurance providers 17, and IUD manufacturers 26. Non-limiting examples of such information stored in the user account database 23 are name, address, contact phone number, contact email address, and participant type. The participant type is an attribute (indicator) for determining which portions of the prescription fulfillment system 11 they may be allow to access. For example, if the participant type is a patient, the patient can view and track the prescription but would be restricted from creating a prescription. The user account information may be provided by each participant via the front-end application 21.

The patient database 22 is configured to store information associated with the patient 12. Non-limiting examples of such information are patient's demographic profile, biometric measurement information, patient's medical history, and family medical history. The patient's demographic profile includes all information relevant to the patient 12 such as name, age, gender, address, phone number, email address, etc. Medical history includes all pertinent medical history of the patient 12 such as treating medical professional information, current prescriptions, allergies, past and current medical conditions, family medical history, etc. The information stored in the patient database 22 may be provided by the patient 12 and/or treating medical professional 20 via the front-end application 21.

The insurance information database 27 is configured to store information associated with the insurance provider 17 and insurance benefit plan of the patient 12. Non-limiting examples of such information are primary insurance provider name, primary insurance provider address, primary insurance plan, primary insurance group number, primary insurance copayment information, primary insurance deductible information, primary insurance contact phone number, primary insurance contact email, secondary insurance provider name, secondary insurance provider address, secondary insurance plan, secondary insurance group number, secondary insurance copayment information, secondary insurance deductible information, primary insurance contact phone number, and primary insurance contact email. The insurance information may be provided by the insurance provider 17 and/or the patient 12 via the front-end application 21.

The medical information database 24 is configured to store necessary information for the medical professional 20 to formulate diagnosis, treatment, and/or prescription. Non-limiting examples of the information stored in the medical information database 24 are disease information, symptom information, and treatment information for various diseases.

The prescription database 25 is configured to store prescription information provided by the medical professional 20 and electronic prescriptions generated via the prescription fulfillment system 11. Non-limiting examples of the information stored in the prescription database 25 are drug name, dosage, amount, refill authorization, refill availability, and patient information.

The alert notification database 29 is configured to store details associated with various alert notifications that may be generated by the prescription fulfillment system 11 and transmitted to various participants 12, 17, 20, 26. Non-limiting examples of the information stored in the alert notification database 27 are alert sent date, sender name, recipient name, alert message, and user type.

The plurality of databases 22, 23, 24, 25, 27, 29 may be configured with any database type such as a relational database, a distributed database, an object database, an object-relational database, NoSQL database, etc. In addition, two or more of the databases 22, 23, 24, 25, 27, 29 may be combined.

The database management system 19 may be of any electronic, non-transitory form configured to manage the plurality of databases 22, 23, 24, 25, 27, 29. The database management system 19 may reside on the same or different computing device from the CPUs 104. The database management system 19 may include MySQL, MariaDB, PostgreSQL, SQLite, Microsoft SQL Server, Oracle, SAP HANA, dBASE, FoxPro, IBM DB2, LibreOffice Base, FileMaker Pro, Microsoft Access, and InterSystems Cache. All or a portion of the database management systems 19 may be maintained by a third party and/or configured as cloud storage.

As stated above, the prescription fulfillment system 11 also includes the front-end application 21. The front-end application 21 may be installed on the participant's computing device 39 for viewing and managing data/information and communicating between the participants 12, 17, 20, 26 of the prescription fulfillment system 11. Thus, the front-end application 19 may be configured to provide for outputting information to the participants 12, 17, 20, 26. More specifically, the front-end application 21 is provided with a graphical user interface (GUI) configured to be displayed on a display device, printer-ready output, display-ready output, and/or audible output. The front-end application 21 may be operatively linked to the network-enabled control system 18 through a network, such as a network 43 of global computers (e.g., the Internet).

The front-end application 21 may be implemented as a stand-alone application on both a web-based platform (online/Internet web application) and mobile-based platform (mobile application) such that the participants 12, 17, 20, 26 may access it over the Internet using a computing device 39 which includes a display and an input device implemented therein. Non-limiting examples of computing devices include a personal computer (laptop or desktop), mobile phone (smartphones), tablets, personal digital assistants (PDA), or other similar devices. The computer devices will typically access the prescription fulfillment system 11 directly through an Internet service provider (ISP) or indirectly through another network interface.

As stated above, the participants 12, 17, 20, 26 of the prescription fulfillment system 11 are the patient 12, medical professional 20, insurance provider 17, and IUD manufacturer 26. The prescription fulfillment system 11 is designed and configured to determine the user type when a participant logs into the prescription fulfillment system 11 with the authentication credentials established (e.g., username and password). Once the user type is determined with a successful login, the prescription fulfillment system 11, according to the embodiment of the present invention, displays information/data that are pertinent to the particular participant type and provides necessary features to perform tasks. For example, all participants 12, 17, 20, 26 may view the prescriptions associated with the patient 12, but a prescription may be processed and created by only the medical professional 20 via the prescription fulfillment system 11.

Figure 5:
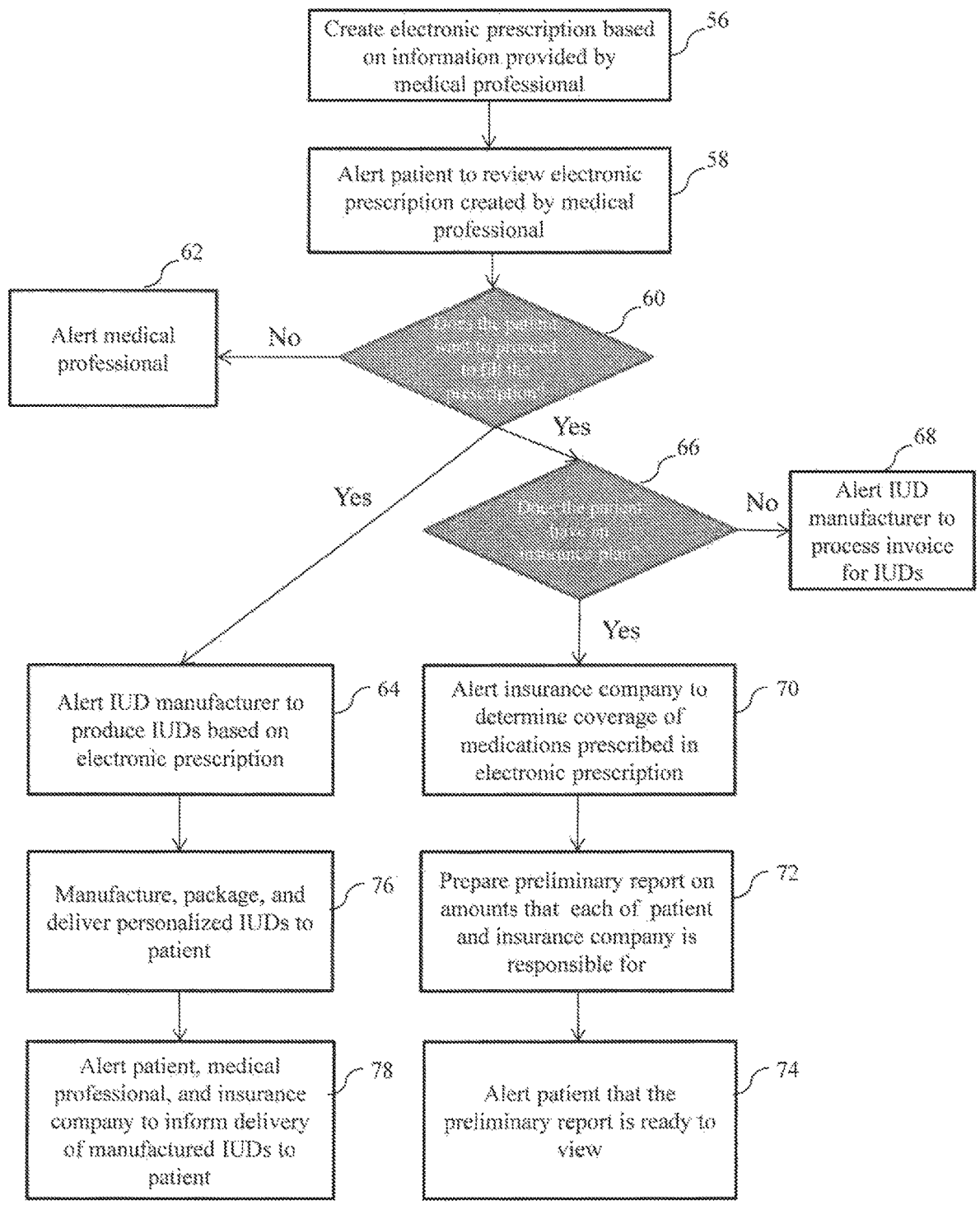
FIG. 5 is a flowchart of a method for electronically creating a prescription and filling the prescription by manufacturing personalized IUDs according to the specification of the prescription.

With reference to FIG. 5, a process for electronically creating a prescription and filling the prescription by manufacturing IUDs according to the specification of the prescription is described in the flowchart. The process includes the steps of electronically creating a prescription based on information provided by the medical professional 20, determining whether to proceed to fill the prescription, verifying patient's insurance plan and determining coverage of the medications prescribed in the prescription based on the patient's insurance plan, manufacturing IUDs based on the prescription by the IUD manufacturer 26, and delivering the manufactured IUDs to the patient 12. All of these steps will be performed using the prescription fulfillment system 11 according to the present invention. These steps will be described in greater detail below.

The medical professional 20 may utilize the prescription fulfillment system 11 to formulate, manage, and track prescriptions for a plurality of patients and communicate data and information (e.g., prescriptions) with other participants of the prescription fulfillment system 11. For example, once the medical professional 20 is authenticated and logged into the prescription fulfillment system 11 via the front-end application 21, the medical professional 20 may access a prescription generation page 49 to manage (view, update, and/or delete) any previously created prescriptions that are stored in the prescription fulfillment system 11.

In addition, the medical professional 20 may electronically prescribe medications and electronically create a prescription for the patient 12 via the prescription generation page 49 in step 56. However, before prescribing medications, the medical professional 20 may need to review information stored in the plurality of databases 22, 23, 24, 25, 27, 29 that are pertinent to the patient 12. To conveniently provide and retrieve the information associated with the patient 12, a patient search feature is provided on the prescription generation page 49 for the medical professional 20 to initiate a patient search to retrieve all information related to the patient 12 before electronically prescribing medications. Non-limiting examples of the patient-specific information are patient's demographic information (e.g., name, age, sex, date of birth, address, etc.), medical history including current medical conditions (e.g., existing symptoms, allergies, and diseases), comprehensive biometric measurement information, including DNA information, collected from the patient 12 and processed by the biometric measurement processing module 31, prescription history, and family medical history.

Once the patient search is completed, a selectable list of drugs may also be provided along with the patient-specific information. The drugs included in the drug list are retrieved according to the patient's current medical conditions, biometric measurement information obtained and collected from the patient 12, and information in the medical information database 24 that are pertinent to the biometric measurement information, for which the drugs may be effective in treating the patient 12. Then, the medical professional 20 may navigate the drug list and select/deselect one or more drugs that may be most effective in treating the patient 12.

The prescription generation page 49 also provides an input field and/or a drop-down list for the medical professional 20 to manually enter and/or select any information that is necessary for the IUD manufacturer 26 to fill the prescription, such as dosage rate and amount for each selected drug, refill authorization, refill availability, etc. Furthermore, the medical professional 20 may manually enter medication instructions (e.g., dosage, frequency, before/after meal instruction, etc.) for the patient 12, which may be retrieved via the mobile device 15 to guide the patient 12 before taking the medications, as described above in connection with the system 10 for making personalized IUDs.

Alternatively, if the medical professional 20 believes that the drug list does not include the most effective drug to treat the patient 12, the medical professional 20 may provide one or more drugs by manually typing in the drug names or some other drug identifiers on the prescription generation page 49.

An IUD manufacturer may be determined and assigned depending on whether the selected/entered drug by the medical professional 20 is a brand name drug or a generic drug. If the selected/entered drug is determined to be a brand name drug, the manufacturer of the selected/entered brand name drug may be automatically assigned via the prescription processing module 33 to make the personalized IUDs based on the specification of the prescription. Whereas, if the selected/entered drug is determined to be a generic drug, the medical professional 20 may assign an IUD manufacturer that may be best suited to produce the selected/entered generic drug.

Once the medical professional 20 has selected and entered all information necessary for electronically generating the prescription and before submitting the information to the prescription fulfillment system 11 via the front-end application 21, the prescription fulfillment system 11 may validate the prescription information provided by the medical professional 20. Specifically, the prescription processing module 33 is utilized to determine if all required prescription information have been provided by the medical professional 20 and if all the prescription information have been selected and entered correctly by the medical professional 20.

If all of the prescription information provided by the medical professional 20 contain no errors and are validated by the prescription processing module 33, the information are transmitted and processed for storing in the prescription database 25 in the database management system 19. Then, the prescription may be electronically generated via the prescription processing module 33 of the networked-enabled control system 18 and, upon request, may be displayed via the front-end application 21.

In step 58, once the new prescription is electronically created by the prescription fulfillment system 11, a new prescription alert notification may be automatically generated and transmitted to the patient 12 via an alert notification module 37 of the network-enabled control system 18. The new prescription alert notification informs the patient 12 that the new prescription has been created and is ready to be reviewed by the patient 12.

The patient 12 may log into the prescription fulfillment system 11 via the front-end application 21 to access a patient page 51 to conveniently view and track all of the patient's prescriptions and medications. Specifically, the patient page 51 displays a comprehensive selectable list of the patient's prescriptions, including the new or unfulfilled prescription, a comprehensive selectable list of the patient's medications, and delivery status of all manufactured personalized IUDs for the patient 12. The patient page 51 may include a search feature which allows the patient 12 to search the list of medications by a medication attribute such as current medications, past medications, IUD manufacturer, specific medication, etc. Once the patient 12 narrows the list of medications, the patient 12 may navigate and select a specific medication to retrieve medication information and medication instructions provided by the medical professional 20. This is an alternative method to the QR code method described above in connection with the system 10 of making personalized individual unit doses (IUDs), for the patient 12 to review the medication instructions before taking the personalized IUDs.

The patient page 51 may also be utilized to search the list of the patient's prescriptions to display prescriptions by a prescription attribute such as unfulfilled prescriptions, fulfilled prescriptions, prescriptions prescribed by the medical professional 20, specific prescription, etc. Thus, in order for the patient 12 to review the alerted new prescription, the patient 12 may search the list of the prescriptions to display only the unfulfilled prescriptions.

The patient page 51 may further include a status indicator for each prescription displayed on the page 51 that allows the patient 12 to update the status of each prescription. For example, depending on the action of the patient 12 on the patient page 51, the status of the prescription may be updated to "review initiated", "proceed to fill" or "not to fill".

In step 60, the patient 12 may review the alerted new prescription via the front-end application 21 and decide whether to proceed to fill the alerted new prescription. If the patient 12 decides not to proceed with the prescription, in step 62, a not-to-fill prescription alert notification may be automatically generated and transmitted via the alert notification module 37 to the medical professional 20, informing that the patient 12 has decided not to proceed to fill the alerted new prescription.

If the patient 12 decides to proceed to fill the alerted new prescription, in step 64, an IUD manufacturing process alert notification may be automatically generated and transmitted via the alert notification module 37 to the IUD manufacturer 26 to initiate production of personalized IUDs based on the alerted new prescription.

Concurrently, in step 66, the prescription fulfillment system 11 may determine, via the insurance processing module 35, if the patient 12 is enrolled in an insurance benefit plan offered by the insurance provider 17, based on the information stored in the insurance information database 27 in the database management system 19.

If the insurance processing module 35 determines that the patient 12 is not enrolled in the insurance benefit plan, in step 68, a no-insurance alert notification may be automatically generated and transmitted via the alert notification module 37 to inform the IUD manufacturer 26 that the patient 12 has no insurance plan. Also, the no-insurance alert notification may instruct the IUD manufacturer 26 to process and send an invoice directly to the patient 12.

When the insurance processing module 35 determines that the patient 12 is enrolled in the insurance benefit plan, in step 70, an insurance alert notification may be automatically generated and transmitted, via the alert notification module 37, to instruct the insurance provider 17 to initiate a process to verify the insurance plan and determine the coverage of the medications prescribed in the alerted new prescription based on the patient's insurance plan.

Using the patient page 51, the patient 12 may also easily manage the existing prescriptions that need to be refilled. As stated above, when the patient 12 selects a prescription, prescription details, including refill authorization and refill availability, are retrieved and displayed on the patient page 51. Thus, if the selected prescription is authorized to be refilled and the refill is available, the patient 12 may simply transmit a refill alert notification via the alert notification module 37 to the IUD manufacturer 26 to create personalized IUDs based on the specification of the prescription. However, if neither the prescription is authorized to be refilled nor the refill is available, the patient 12 may transmit a refill request alert notification via the alert notification module 37 to the medical professional 20 to request a new prescription. In this case, the medical professional 20 may simply process a new prescription via the prescription fulfillment system 11 or may require the patient to transmit current biometric measurement information via the wearable and/or non-wearable biometric measurement modules 14, 16 and/or request the patient to visit the medical professional's office to evaluate patient's current medical conditions before processing a new prescription.

The insurance provider 17 may log into the prescription fulfillment system 11 via the front-end application 21 and access a patient prescription page 53 to view and track all prescriptions for the patients who are enrolled in the insurance benefit plans offered by the insurance provider 17.

Specifically, the patient prescription page 53 may display a comprehensive selectable list of the patients' prescriptions, including new or unfulfilled prescriptions. Similar to the patient page 51, the patient prescription page 53 includes a search feature which allows the insurance provider 17 to narrow the list and display prescriptions by a prescription attribute such as new prescription, fulfilled prescription, prescriptions prescribed by the medical professional 20, prescriptions for the patient 12, specific prescription, etc. Thus, in order for the insurance provider 17 to determine the coverage of the medications prescribed in the alerted new prescription of the patient 12, the insurance provider 17 may filter the list of the prescriptions to include only the new prescriptions.

When the insurance provider 17 selects one of the new prescriptions from the filtered list, patient-specific information, insurance information, and prescription information related to the selected prescription are displayed. Non-limiting examples of the patient-specific information, insurance information, and prescription information are patient's name, address, insurance provider name, insurance plan, drug names, and refill authorization.

Then, in step 72, the insurance provider 17 may compare the medication charges with the terms of the patient's insurance benefit plan and coverage, and prepares, via the insurance processing module 35, a preliminary amount report that includes the amount that the patient owes (e.g., deductibles and copayments if applicable), as well as the amount that the insurance provider 17 is financially responsible for. An insurance coverage alert notification is then generated and transmitted via an alert notification module 37 of the network-enabled control system 18 to the patient 12 in step 74, informing the preliminary amount report is saved and stored in the prescription fulfillment system 11 for the patient 12 to view via the front-end application 21.

The patient prescription page 53 may further include a status indicator for each prescription displayed on the page 53 that allows the insurance provider 17 to update the status of the prescription. For example, depending on the activity of the insurance provider 17 on the patient prescription page 53, the status of the prescription may be updated to "insurance coverage analysis initiated", "insurance coverage analysis completed", "preliminary amount report initiated", or "preliminary amount report initiated".

The IUD manufacturer 26 may also login into the prescription fulfillment system 11 via the front-end application 21 and access a prescription fulfillment page 55 to view and manage (update) all prescriptions that are assigned to the IUD manufacturer 26. Specifically, the prescription fulfillment page 55 displays a comprehensive selectable list of all the assigned prescriptions, including new or unfulfilled prescriptions that are stored in the prescription fulfillment system 11. Similar to the patient page 51 and patient prescription page 53, the prescription fulfillment page includes a search feature that allows the IUD manufacturer 26 to narrow the list by a prescription attribute such as fulfilled prescriptions, unfulfilled prescriptions, prescriptions prescribed by the medical professional 20, prescriptions for the patient 12, etc. Thus, in order to manufacture personalized IUDs and fill the alerted new prescription, the IUD manufacturer 26 may filter the list of the assigned prescriptions to only display the unfulfilled prescriptions.

When the IUD manufacturer 26 selects the alerted new prescription from the filtered list, patient-specific information and prescription information related to the selected prescription are displayed so that the IUD manufacturer 26 may be able to manufacture the IUDs according to the specification of the alerted new prescription. Non-limiting examples of the patient-specific information and prescription information are patient's name, address, allergies, drug names, dosage and amount, and medication instructions provided by the medical professional 20.

After the IUD manufacturer 26 fills the alerted new prescription by manufacturing the personalized IUDs, in step 76, the IUD manufacturer 26 proceeds to package the manufactured personalized IUDs and validate that every manufacturing process has been complied and performed correctly before shipping them directly to the patient 12.

In step 78, a delivery alert notification may be automatically generated and transmitted to the patient 12, medical professional 20, and insurance provider 26 via the alert notification module 37, informing the shipment of the personalized IUDs and expected arrival date.

For packaging and delivery, the prescription fulfillment system 11 may implement the same features and methods as described above in connection with the system 10 of making personalized IUDs.

The prescription fulfillment page 55 may further include a status indicator for each prescription displayed on the page 55 that allow the IDU manufacturer 17 to update the status of the prescription. For example, depending on the activity on the prescription fulfillment page 55, the status of the prescription may be updated to "production initiated", "production completed", "packaging initiated", "packaging completed", and "IUDs shipped".

Biometric Measurements and Devices

The system for creating one or more personalized individual unit doses (IUDs) 10 and prescription fulfillment system 11 may use a wide variety of measurement tools to provide the necessary information for a medical professional to formulate a one or more of a diagnosis, treatment, regimen and prescription. The network-enabled control system 18 uses biometric measuring instruments to take measurements in accordance with instruction from the medical professional and to communicate these measurements via the control network to the medical professional. For example, in one aspect of this disclosure, an individual telecommunicates, e.g., using live video conferencing, to allow the medical professional to evaluate the individual's current condition and perform a virtual exam. The medical professional may conduct an examination in a similar fashion to an in-office exam, asking the appropriate questions necessary for a medical diagnosis, and may instruct the patient to take certain measurements using available equipment, such as availing him or herself of the biometric module(s). The medical professional may request results of the measurements to be input and sent via a computer device, communicated by direct observation of the medical professional, or orally communicated by the patient to the medical professional. Regardless of the means of receiving the medical data from the patient, the medical professional is able to determine a diagnosis or at least make a medical finding sufficient to recommend one or more of, a course of treatment, regimen and/or prescribe an appropriate prescription of IUDs.

The US Centers for Disease Control and Prevention defines biometric screenings as the measurement of physical characteristics such as height, weight, BMI, blood pressure, blood cholesterol, blood glucose, and aerobic fitness that can be taken outside of a medical professional's office or hospital, for example at the home or a worksite, and which may be used as a stand-alone or part of a health assessment. The use of biometrics in the present personalization system is to allow the streamline the process of an individual patient's medical assessment and fast, efficient and cost effective production and delivery of the prescribed IUD directly to those in need. Such efficiency further serves to lower the overall costs of medical care on a patient-to-patient basis, allows for a minimum of inventory, and hence a minimum of shelf life.

The networked-enabled control system desirably includes a processor, memory storage, and executable instructions, as further shown in FIG. 3. Optionally, the system includes one or more of a display device (s), an alpha-numeric input device(s), a cursor control device(s), a drive unit(s), a machine-readable medium(s) device(s) and a signal generation device(s). The biometric measurement devices desirably, but not necessarily, interface with the processor, to facilitate the transfer of biometric measurements, although manual input of the measurement data collected and/or measured using the biometric measurement device is also contemplated. A software program and forms designed to provide a template for entering data and information useful for the medical professional may also be included as part of the system.

The biometric measurement module may include an invasive device and/or non-invasive measurement device, or a combination thereof. The biometric measurement module may include a device selected from the group consisting of acoustical instruments, visual instruments, tactile instruments, chemical instruments, biological instruments, electrical instruments, thermal instruments and combinations thereof. The biometric measurement module may include a device selected from the group consisting of cameras, video scopes, illumination systems, colorimeters, spirometers, holter monitors, vital sign monitors, signal monitors, sensors, ultrasound probes, machines which measure electric signals from the body, blood chemistry instruments, blood flow measurement devices, blood content measurement devices, thermal measurement devices and combinations thereof. The biometric measurement module may include a device selected from the group consisting of electroencephalogram (EEG) machines, electrocardiogram (EKG) machines, electromyogram (EMG) machines, echocardiogram (ECG) machines, atrial fibrillation devices, stethoscopes, pharyngoscopes, sinus scopes, otoscopes, laparoscopes, dermascopes, blood gas measurement devices, multi-purpose cameras, retinal cameras, ocular measurement devices, intraoral cameras, abdominal ultrasound devices, vascular ultrasound devices, trans-vaginal ultrasound devices, skin surface measurement devices which measure one or more of temperature, blood flow, blood sugar, skin color, skin texture, blood-fat content, blood cholesterol content; accelerometers, movement sensors, and combinations thereof.

Examples of biometric measurement instruments include, without limitation, acoustical instruments, visual instruments, tactile instruments, chemical instruments, biological instruments, electrical instruments and combinations thereof. For example, useful biometric instruments include those selected from cameras, video scopes, illumination systems, colorimeters, spirometers, holter monitors, vital sign monitors, signal monitors, sensors, ultrasound probes, machines which measure electric signals from the body, blood chemistry instruments, blood flow measurement devices, blood content measurement devices, thermal measurement devices and combinations thereof. More specifically, the device for measuring biometrics may be is selected from electroencephalogram (EEG) machines, electrocardiogram (EKG) machines, heart rate monitors, electromyogram (EMG) machines, echocardiogram (ECG) machines, atrial fibrillation devices, stethoscopes, pharyngoscopes, sinus scopes, otoscopes, laparoscopes, dermascopes, blood gas measurement devices, multi-purpose cameras, retinal cameras, ocular measurement devices, intraoral cameras, abdominal ultrasound devices, vascular ultrasound devices, trans-vaginal ultrasound devices, skin surface measurement devices which measure one or more of temperature, blood flow, blood sugar, skin color, skin texture, blood-fat content, blood cholesterol content; accelerometers, movement sensors, and combinations thereof.

The biometric measurement module may also include a mobile device including one or more software applications that may be used to obtain biometric information, information which is used in making a diagnosis, information used in the medical evaluation, information used in evaluating the treatment effectiveness and/or change in treatment necessary for the individual, or a combination thereof. Such mobile devices may include a mobile phone, tablet, laptop, watch or wearable device. In some instances, the device may be an implant located on or within the body of the individual patient.

Desirably, the medical professional is able to read the results directly from the measurement instrument via video conferencing, but alternatively, the results may be communicated to the medical professional via the internet, orally communicated, or by a recording of the results sent through the network. The virtual exam desirably proceeds in much the same way as an in-office exam does, and desirably results in a recommended course of treatment, a regimen or a prescription which is communicated/provided to the patient. In the case where a prescription for an IUD of medication is generated, the prescription is communicated, desirably electronically, to the manufacturer of the IUD, where the IUD is then made in accordance with the prescribed dosage form (e.g. film, tablet, capsule, solution, cream, patch, syrup etc.) and prescribed dose, for example, 1 mg, 2 mg, 5 mg, 10 mg, 20 mg, 30 mg, 40 mg, 50 mg, 60 mg, 70 mg, 80 mg, 90 mg, 100 mg, 150 mg, 200 mg, 500 mg, 1000 mg and various amounts in between, or even higher, depending on a number of factors, including but not limited to the chosen active, the patient's medical condition, patient history and the prescribed regimen or treatment. For example, the prescription may call for IUDs of oral films containing 10 mg of a CNS drug, or tablets containing 500 mg of an analgesic drug. The manufacturer then makes the personalized prescription to order and delivers (sends) it to the individual for whom it is prescribed. Alternatively, delivery may be to an intermediary for quality check, or for further distribution to the individual.

Manufacturing the IUDs may be performed by or under the supervision of any licensed manufacturer of the active and the dosage forms, or a pharmaceutical compounder. However, unlike the conventional system, where compounded medications are made by a licensed pharmacist in a pharmacy based on a prescription, according to the present invention, the manufacturer can make the personalized IUD based on a medical prescription and/or health information obtained via a networked system, and then the personalized IUD can be delivered directly to the patient, all through the disclosed system.

Manufacturing the IUD may include one or more of the following steps: providing a carrier matrix to one or more of the apparatus for making the personalized IUD; providing the active to one or more of the apparatus; combining the active and carrier matrix in one or more of the apparatus; forming the IUD from the carrier matrix and the active; and packaging the IUD for distribution to the individual. Any packaging known for use in the art with pharmaceutical products may be used herein.

Dosage Forms

Any dosage form may be useful in the present disclosure. For example, useful non-limiting dosage forms include oral films (including rapid-dissolve film products), wafers, capsules, tablets, suspensions, solutions, ointments, patches, creams, gels, troches, ampules, vials, syrups, tinctures, spirits, lozenges, balms, liniments, injectables and combinations thereof. Currently, as required by various world regulatory authorities, dosage forms may not vary in the amount of active present by more than specified percentages from the desired amount (labelled amount). When applied to dosage units based on the dosage forms recited herein, this virtually mandates that uniformity of active content in the dosage form as compared to the labelled amount (i.e., desired amount) be present.

These dosage forms for use in this disclosure may be made by any means known in the art. Examples of methods of making capsules which are useful herein are described in U.S. Pat. Nos. 5,795,590 and 4,738,817, which are incorporated herein in their entirely. Examples of methods of making tablets which are useful in the present invention are described in U.S. Pat. Nos. 5,213,738, 5,456,920 and 5,437,872, contents of each are incorporated herein in there entirety. Further descriptions of useful methods of making tablets are described in "Pharmaceutical Dosage Forms: Tablets Volume 1," Edited by Herbert A. Lieberman and Leon Lachman, Marcel Dekker, Inc, 1980, the contents of which are fully incorporated by reference herein.

Films

In the case of oral film dosage forms, the formation of agglomerates is to be avoided because they tend to randomly distribute the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount(s) of active(s) for the recommended treatment. Failure to achieve a high degree of accuracy with respect to the amount of active ingredient in the cut film can be harmful to the patient. For this reason, dosage forms formed by conventional processes such as described by U.S. Pat. No. 4,136,145 to Fuchs, et al. ("Fuchs"). Fuchs, would not likely meet the stringent standards of governmental or regulatory agencies, such as the U.S. Federal Drug Administration ("FDA"), relating to the percent of active which may vary in dosage forms compared to the labelled amount of active.

Oral films for use in this disclosure may be made by any means known in the art. Examples of methods of making oral films including those describing uniformity of active content, preparing proper dosages and optimizing film processes, packaging administering IUDS, which are useful herein are described in U.S. Pat. Nos. 7,425,292; 7,357,891; 7,666,337; 8,017,150; 8,603,514; 8,765,167; 8,906,277; 8,900,497; 9,855,221; 9,931,305; 8,393,255 (pouch cutter); U.S. Pat. Nos. 8,298,583 and 8,663,696 (tetrahydrolipastatin films);U.S. Patent Application Publication No. 2012/0107402A1(Process for analyzing and establishing dosage size in an ingestible film); U.S. Pat. No. 8,282,954 (making film using a slurry with no water-based components i.e., only organic solvents); U.S. Pat. No. 9,095,577 (stabilized amine systems); U.S. Pat. No. 9,095,495 (device for administering effective dosages); U.S. Pat. No. 8,577,488 (optimizing film scrap); U.S. Pat. Nos. 8,936,825 and 9,561,191 (forming film directly onto the package); U.S. Pat. No.

8,974,826 (nanoparticle film delivery systems); U.S. Pat. Nos. 8,790,704 and 9,474,687 (peptide nanoparticle films); U.S. Pat. Nos. 9,346,601 and 9,771,173 (Reduction in stress cracking of films); U.S. Pat. Nos. 8,241,661 and 8,617,589 (Biocompatible Film With Variable Cross-Sectional Properties), all assigned to Aquestive, Inc., (formerly MonoSol Rx, LLC), all of which are incorporated herein in their entirely.

Uniformity of Content

Each IUD must meet the uniformity of content requirements which assure that a defined amount of active will be in each IUD. The IUDs are labeled with a specific desired amount of active in each IUD. The IUDs are manufactured such that the finished IUD product will contain an active content which does not vary more than 10% for the desired amount. For example, if the desired amount (labeled amount) of active in an IUD is 100 mg, then the IUDs may vary from 90 mg to 110 mg in the amount of active, but desirably not outside of this range.

Health Information of the Individual

As discussed herein, the invention includes the use of a device for measuring biometric information of the individual. The information may be seen by or transmitted directly to the medical professional, or alternatively, it may be stored in the networked control system and accessed at a later date by the medical professional or the patient. Additionally, the networked system may be configured to link to and/or data transfer with one or more third party information data bases containing patient information, information related to diagnosis, disease states, prior patient histories, treatment protocols for disease or medical conditions and manufacturers of IUDs.

This individualized system is able to specifically take into account diverse backgrounds such as computational biology, bioinformatics, computer science, biology, pharmacology, medicine and biomedical engineering, when formulating the personalized IUD for each individual patient.

A prescription drug monitoring program (PDMP) is an electronic database that tracks controlled substance prescriptions in a state. PDMPs can provide health authorities timely information about prescribing and patient behaviors that contribute to the prescription drug epidemic and facilitate a targeted response. PDMPs are one of the most promising tools available to address prescription opioid misuse and abuse. PDMPs operate in every state (except Missouri) to collect data from pharmacies on controlled prescription drugs dispensed to patients. Pharmacists (and some dispensing physicians) report to a PDMP each time a prescription is filled for a controlled substance medication. When available at the point of care, information from the PDMP can give a prescriber or pharmacist critical information regarding a patient's history with prescription drugs. Providers are more easily able to distinguish between patients who legitimately need opioid medications for treatment and those who may be seeking to misuse the drugs. Reviewing PDMP data before prescribing also provides an opportunity to intervene early if there are signs of misuse or abuse. Additionally, licensing and regulatory boards can use PDMP data to identify unusual prescribing patterns by prescribers.

Accordingly, the system or method of the disclosure may optionally employ review of the PDMP data prior to determining the medical prescription and making the IUD. It may also include the step of providing and/or storing information (i.e., data) related to the individual's health history, including individualized information on safety, efficacy, side effects, frequency of use of an active. Because the system disclosed herein already involves a networked system, this additional check may be a seamless and fluid part of the operation.

Film IUD

In an embodiment, the personalized IUD is a film. The film may be any known film in the art used for delivery of a pharmaceutical active.

In one aspect, the film is a rapid-dissolve dosage form for drug delivery whereby the active agents are taste-masked or controlled-release coated particles. In film dosage forms, the taste-masked agents are desirably uniformly distributed throughout the large sheets of film which are then cut into IUDs. The rolls of films made for use in this invention can be divided into equally sized individual unit dosages having substantially equal amounts of each active component present. This advantage is particularly useful because it permits large area films to be initially formed, and subsequently cut into individual unit dosages without concern for whether each unit contains a substantially uniform content of active Pharmaceutical film dosage forms have only relatively recently been marketed largely due to the inability to achieve drug content uniformity in the large area films and thus in the IUDs cut therefrom. Thus, for example, the films of the present disclosure have particular applicability as pharmaceutical dosage delivery systems because each individual unit dose of film will contain the proper predetermined amount of drug, which will not vary more than 10% from the desired amount, i.e. the labelled amount.

In a further aspect of the present invention, methods of forming the films of this invention are provided, by wet casting methods and hot melt extrusion methods. In a wet casting method, the film product is formed by combining a polymer and a polar solvent, forming the combination into a film, and drying the film in a controlled manner. Preferably, the film is dried initially only applying heat to the bottom side of the film, in order to maintain a non-self-aggregating uniform heterogeneity. Desirably, during the initial bottom drying stage, substantially no convection currents, i.e., hot air currents, are permitted to travel across the top of the film until the visco-elastic properties of the film are such that the film components are "locked" in place and cannot move to cause non-uniformity. At that stage, other methods of heating to effect drying may be employed.

The films may be formed with a polar solvent which may be water, a polar organic solvent, or a combination thereof. An active ingredient may be added to the polymer and water combination prior to the drying step. Alternatively, or in addition to controlling the drying the film, the polymer may be selected in order to provide a viscosity that maintains the non-self-aggregating uniform heterogeneity. Moreover, the composition desirably is mixed in a manner to minimize the incorporation of air into the mixture and is desirably deaerated, such as by conditioning at room temperature, vacuum treatment or the like, to allow trapped air to escape prior to the drying process. This serves to eliminate bubble and void formation in the final film product, thereby further improving uniformity. Reverse roll coating is one particularly useful coating technique may also be used to form the film.

Another embodiment of the present invention may include a rapid-dissolve film product containing at least one water-soluble polymer including polyethylene oxide alone or in combination with a hydrophilic cellulosic polymer, wherein the film product may be free of added plasticizers. Preferably, the rapid-dissolve film product includes at least one water-soluble polymer containing about 20% to 100% by weight polyethylene oxide, about 0% to 80% by weight hydroxypropylmethyl cellulose, and about 0% to 80% by weight hydroxypropyl cellulose; an active component; sweetener; at least one flavoring; and at least one colorant, wherein the film product optionally is free of added plasticizers, surfactants, and polyalcohols.

In another aspect of the present invention, the films employing polyethylene oxide as the film-forming polymer may be formed by a hot melt extrusion process, whereby an edible film-forming polymer is provided, and active components are added during manufacture, and the mixture is blended at elevated temperature in the absence of additional solvent to form a uniform matrix, and extruded to form a film. Desirably, the film will be further shaped by rollers to a specified thickness, and allowed to cool and harden to form a self-supporting film. A particularly desirable film forming polymer for extrusion manufacture is polyethylene oxide, which is heated to about 65° C. to about 80° C. during blending to provide a pliable uniform matrix. The extrusion may be accomplished with a single screw extrusion apparatus or other suitable extrusion apparatus.

A particular advantage of the aforementioned extrusion processes when employed with particulate coated active ingredients is that the absence of additional solvent during the manufacturing process lessens the likelihood of dissolution or release of the taste-masked or controlled-release coated active agent during manufacture due to dissolution or solvent effects.

Another aspect of the present invention provides films containing coated particles that include an active agent and a taste-masking and/or controlled-release coating. Accordingly, there is provided a drug delivery composition that includes (i) a flowable water-soluble film forming matrix; (ii) a particulate bioeffecting agent uniformly stationed therein; and (iii) a taste-masking agent or controlled-release agent coated or intimately associated with the particulate to provide taste-masking of the bioeffecting agent. In some embodiments, the combined particulate and taste-masking agent have a particle size of 200 microns or less and the flowable water-soluble film forming matrix is capable of being dried without loss of uniformity in the stationing of the particulate bioeffecting agent therein.

In some other embodiments, the taste-masking or controlled-release coated particles may have a particle size of 50 to 250 microns, and the flowable water-soluble film forming matrix is capable of being dried without loss of uniformity in the stationing of the particulate bioeffecting agent therein. The importance of particle size is heightened in orally ingestible thin films, where uniformity is also of particular importance, and the prior art has failed to recognize such critically important features.

Desirably, the size of the combined particulate and taste-masking agent have a particle size of 150 microns or less, or 100 microns or less. The flowable water-soluble film forming matrix is formable into a dry film of less than about 380 microns in thickness, for example less than about 250 microns in thickness. Desirably, the coated particles are embedded entirely within the finished films. In other words the dry films of the present invention desirably have smooth surfaces free of exposed agents or coated particles that could impart grittiness or maldistribution of the active. Thus, in one aspect of the invention there is provided a film vehicle which contains a uniform distribution of actives, as defined herein, being suitably free of particles which accumulate on the film surface when dried.

Desirably, the taste-masking or controlled-release agent is a thin film coating over portions of the bioeffecting agent. Useful taste-masking agents include polymeric materials. Water-soluble polymers are also useful. Desirably, the water-soluble polymer has an average molecular weight of equal to or greater than about 40,000. Furthermore, water-soluble polymers may be acrylic polymers, cellulosic polymers, and combinations thereof. Additionally, vinyl polymers, crown ethers, hydrogenated oils and waxes, and combinations thereof may also be used as taste-masking agents.

In some embodiments described herein, a thin film drug delivery composition includes: (a) an edible water-soluble film forming matrix; and (b) a coated particulate active component uniformly stationed therein, wherein the coating on the particulate active component is a taste-masking or controlled-release agent and wherein the coated particulate active component has a particle size of 50 to 250 microns and is uniformly distributed in the film composition.

In some other embodiments, there is provided a thin film drug delivery composition, which includes: (a) an edible water-soluble film forming matrix including at least one water-soluble polymer including polyethylene oxide alone or in combination with a hydrophilic cellulosic polymer; and (b) a coated particulate active component uniformly stationed therein, wherein the coating on the particulate active component is a taste-masking and/or controlled-release agent, and wherein the active component is uniformly distributed in the film composition.

Polymers Useful in the Manufacture of IUDs

Polymers useful in the manufacture of IUDs may employ a polar solvent, such as water or alcohol, during the manufacturing process to soften or dissolve the polymeric materials. Preferably, the polymers will be water soluble. As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or other dosage forms of the present invention formed from such water soluble polymers are desirably sufficiently water soluble to be dissolvable upon contact with bodily fluids.

Other polymers useful for incorporation into the films or other dosage forms of the present invention include biodegradable polymers, copolymers, block polymers and combinations thereof. Among the known useful polymers or polymer classes which meet the above criteria are: poly (glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly (lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.).

The Biodel materials represent a family of various polyanhydrides which differ chemically. Although a variety of different polymers may be used, it is desired to select polymers to provide a desired viscosity of the mixture. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

Among the polymers recited above, polyethylene oxide (PEO), when used alone or in combination with a hydrophilic cellulosic polymer, is particularly suited to hot melt extrusion processes, and achieves flexible, strong films. Additional plasticizers or polyalcohols may optionally be included. Non-limiting examples of suitable cellulosic polymers for combination with PEO include hydroxypropyl cellulose (HPC) and hydroxypropylmethyl cellulose (HPMC). PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg.

In some embodiments of the instant invention, a hydrophilic cellulosic polymer such as HPMC may also be used as a water soluble polymer, in from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC).

Viscosities of Fluid Matrices and Components

The polymer plays an important role in affecting the viscosity of dosage forms such as suspensions, liquids, solutions and films. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. When the dosage form is a film, desirably, the viscosity of the film-forming matrix will rapidly increase upon initiation of the drying process, which is a factor in ensuring particulates of active are substantially "locked-in" place and thus remain substantially uniformly stationed in the matrix in which they are carried.

The viscosity of a carrier matrix may be adjusted based on the selected active depending on the other components within the matrix. Viscosity is particularly important for actives which are particulate in nature. For example, if the component is not soluble within the selected solvent, a proper viscosity may be selected to prevent the component from settling which would adversely affect the uniformity of the resulting film or liquid dosage form. The viscosity may be adjusted in different ways. To increase viscosity of a film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

The carrier matrix may be any known inert component or mixture of components used in the formulation of pharmaceutical components. As readily understood by one of ordinary skill in the art, the carrier matrix differs greatly depending on the dosage form and the desired end product. For example, the carrier matrix may be a formulation comprising polymers, solvents, additives, and/or lubricants. It may include powders, liquids or a combination thereof.

Polymers for Extruded Films

In an alternative embodiment of this invention, hot melt extrusion may be used to form films. For extrusion processes, the polymers must be thermoplastic, meaning the polymers can be melted in a suitable apparatus, blended with other ingredients as desired, and extruded under pressure through an orifice to provide a film.

Active Agents

Suitable actives for use in the self-supporting films herein include, but are not limited to, the following therapeutic classes: ace-inhibitor; adrenergic agent; adrenocortical steroid; adrenocortical suppressant; aldosterone antagonist; alkaloid; amino acid; anabolic; analeptic; analgesic; anesthetic; anorectic; anti-acne agent; anti-adrenergic; anti-allergic; anti-amebic; anti-anemic; anti-anginal; anti-anxiety; anti-arthritic; anti-arrythmia; anti-asthmatic; anti-atherosclerotic; anti-cholesterolemic; antibacterial; antibiotic; anticholinergic; anticoagulant; anticonvulsant; antidepressant; antidiabetic; antidiarrheal; antidiuretic; antidote; antiemetic; anti-epileptic; antifibrinolytic; antifungal; antihemorrhagic; antihistamine; antihyperlipidemia; antihypertensive; antihypotensive; anti-infective (both systemic and non-systemic); anti-inflammatory; anti-lipid; antimanic; antimicrobial; antimigraine; antimitotic; antimycotic, antinauseant; antineoplastic; antineutropenic; anti-obesity; antiparasitic; anti-parkinson; antiproliferative; antipsychotic; anti-pyretic; antirheumatic; antiseborrheic; antisecretory; antispasmodic; anti-stroke; antithrombotic; anti-thyroid; anti-tumor; anti-tussive; anti-ulcerative; antiuricemic; antiviral; appetite suppressant; appetite stimulant; biological response modifier; blood glucose regulator; blood modifier; blood metabolism regulator; bone resorption inhibitor; bronchodilator; cardiovascular agent; central nervous system stimulant; cerebral dilator; contraceptive; coronary dilator; cholinergic; cough suppressant; decongestant; depressant; diagnostic aid; dietary supplement; diuretic; dopaminergic agent; enzymes; estrogen receptor agonist; endometriosis management agent; expectorant; erectile dysfunction therapy; erythropoietic; ibrinolytic; fertility agent; fluorescent agent; free oxygen radical scavenger; gastric acid suppressant; gastrointestinal motility effector; genetic modifier; glucocorticoid; hair growth stimulant; hemostatic; histamine H2 receptor antagonists; homeopathic remedy; hormone; hypercalcemia management agent; hypocalcemia management agent; hypocholesterolemic; hypoglycemic; hypolipidemic; hypotensive; ion exchange resin; imaging agent; immunizing agent; immunomodulator; immunoregulator; immunostimulant; immunosuppressant; keratolytic; laxative; LHRH agonist; mood regulator; motion sickness preparation; mucolytic; muscle relaxant; mydriatic; nasal decongestant; neuromuscular blocking agent; neuroprotective; NMDA antagonist; non-hormonal sterol derivative; osteoporosis therapy; oxytocic; parasympatholytic; parasympathomimetic; plasminogen activator; platelet activating factor antagonist; platelet aggregation inhibitor; prostaglandin; psychotherapeutic; psychotropic; radioactive agent; respiratory agent; scabicide; sclerosing agent; sedative; sedative-hypnotic; selective adenosine A1 antagonist; serotonin antagonist; serotonin inhibitor; serotonin receptor antagonist; smoking cessation therapy; steroid; stimulant; sympatholytic; terine relaxant; thyroid hormone; thyroid inhibitor; thyromimetic; tranquilizer; tremor therapy; amyotrophic lateral sclerosis agent; cerebral ischemia agent; Paget's disease agent; unstable angina agent; vasoconstrictor; vasodilator; weight management; wound healing agent; xanthine oxidase inhibitor; and combinations thereof.

Examples of pharmaceutical actives suitable for use herein include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as oxycodone (commercially available as Oxycontin®); ibuprofen (commercially available as Motrin®, Advil®, Motrin Children's®, Motrin TB®, Advil Children's®, Motrin Infants®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially available as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The self-supporting films disclosed herein may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate agonists and antagonists, such as buprenorphine and naloxone are further examples of drugs for use in the present invention.

Other preferred drugs for other preferred active ingredients for use herein include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful herein include, but are not limited to, alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®)), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Actives for use in the present disclosure may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present disclosure may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as C1 esterase Inhibitor (human) (commercially available as Berinert®) and ecallantide (commercially available as Kalbitor®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

Other actives may further include one or more antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), canakinumab (commercially available as Llaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESIcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The pharmaceutical actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®)), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), exenatide (commercially available as Bydureon®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance® and Fortamet®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), canagliflozin (commercially available as Invokana®), linagliptin (commercially available as Tradjenta®), dapagliflozin (commercially available as Farxiga®), insulin glargine (commercially available as Lantus® or Toujeo®), insulin aspart (commercially available as Novolog®), insulin lispro, empagliflozin (commercially available as Jardiance®), and tolazamide (commercially available as Tolinase®).

Other useful actives of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®), bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Actives useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide(commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Actives useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as haemophilus b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful actives include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

Other actives are useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, Tresiba®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraf®, Neoral®, Sandimmune®, and Apo-Cyclosporine®).

Actives useful in the present disclosure may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril®), tizanidine (commercially available as Zanaflex®), and hyoscyamine sulfate (commercially available as Levsin®).

Actives useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-I b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Actives may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), asenapine (commercially available as Saphris®), iloperidone (commercially available as Fanapt®), paroxtine hydrochloride (available as Paxil®), aripiprazole (commercially available as Abilify®), guanfacine (commercially available as Intuniv®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Actives useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other actives useful herein may include Sleep disorder medications, including zaleplon (available as Sonata®), eszopiclone (available as Lunesta®), zolpidem tartrate (commercially available as Ambien®, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Other actives may be useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular H2-antagonists which are contemplated for use herein include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Examples of specific actives include but are not limited to 16-alpha fluorocstradiol, 16-alpha-gitoxin, 16-epiestriol, 17 alpha dihydroequilenin, 17 alpha estradiol, 17 beta estradiol, 17 hydroxy progesterone, 1alpha-hydroxyvitamin D2,1-dodecpyrrolidinone, 20-epi-1,25 dihydroxyvitamin D3, 22-oxacalcitriol, 2CVV, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecainide Hydrochloride, Aceclidine, aceclofenae, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adipheinine Hydrochloride, adiposin, Adozelesin, adrafinil, Adrenalone, airbutamine, alacepril, Alamecin, Alanine, Alaproclate, alaptide, Albendazole, albolabrin, Albuterol, Albutoin, Alclofenae, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alogliptin, Alonimid, alosetron, Alosetron Hydrochloride, Alovudine, Alpertine, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverinc Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquine, Amodiaquine Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, amrinone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, aripiprazol, arotinolol, Arpinocid, Arteflene, Artilide Fumarate, asimadoline, aspalatone, Asparaginase, Asparic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, betaalethine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimithil, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelains, bromfenac, Brominidione, Bromocriptine, Bromodiphenhydramine Hydrochloride, Bromoxamide, Bromperidol, Bromperidol Decanoate, Brompheniramine Maleate, Broperamole, Bropirimine, Brotizolam, Bucainide Maleate, bucindolol, Buclizine Hydrochloride, Bucromarone, Budesonide, budipine, budotitane, Buformin, Bumetamide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canagliflozin, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-amino-triazo-le, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Camidazole, Caroxazone, carperitide, Carphenazine Maleate, Carprofen, Carsatrin Succinate, Cartazolate, carteolol, Carteolol Hydrochloride, cartilage derived inhibitor, Carubicin Hydrochloride, Carumonam Sodium, carvedilol, carvotroline, Carvotroline Hydrochloride, carzelesin, casein kinase inhibitors (ICOS), castanospermine, caurumonam, cebaracetam, cecropin B, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone Sodium, Ceforamide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetaben Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, Chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besilate, Cisconazole, Cisplatin, cis-porphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxamide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazosin, cyclic HPMPC, Cyclindole, Cycliramine Maleate, Cyclizine, Cyclobendazole, cyclobenzaprine, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, dapagliflozin, daphlnodorin A, dapiprazole, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichliorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, 9-, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin A1, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfiram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadrotil, ecdisteron, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenae, Elucaine, emalkalim, emedastine, Emetine Hydrochloride, emiglitate, Emilium Tosylate, emitefur, emoctakin, empagliflozin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, episteride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated Estrogens, Esterified Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethyndiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprocin Hydrochloride, eveminomicin, Exametazime, examorelin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypres sin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen 1 125, filgrastim, Filipin, finasteride, Flavodilol Maleate, flavopiridol, Flavoxate Hydrochloride, Flazalone, flecainide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracen Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Flurocitabine, Flurofamide, Flurogestone Acetate, Flurothyl, Fluroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenyloin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycopine, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene: Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurca, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, lemefloxacin, lesopitron, Ifetroban, Ifosfamide, Ilepeimide, illimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecainide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazole, Intriptyline Hydrochloride, iobenguane, Iobenzamic Acid, iobitridol, Iocarmate Meglumine, Iocarmic Acid, Iocetamic Acid, Iodamide, Iodine, Iodipamide Meglumine, Iodixanol, iodoamiloride, Iodoantipyrine I 131, Iodocholesterol I 131, iododoxorubicin, Iodohippurate Sodium I 131, Iodopyracet I 125, Iodoquinol, Iodoxamate Meglumine, Iodoxamie Acid, Ioglicic Acid, Iofetamine Hydrochloride I 123, iofratol, Ioglucol, Ioglucomide, Ioglycamic Acid, Iogulamide, Iohexol, iomeprol, Iomethin I 125, Iopamidol, Iopanoic Acid, iopentol, Iophendylate, Ioprocemic Acid, iopromide, Iopronic Acid, Iopydol, Iopydone, iopyrol, Iosefamic Acid, Ioseric Acid, Iosulamide Meglumine, Iosumetic Acid, Iotasul, Iotetric Acid, Iothalamate Sodium, Iothalamic Acid, iotriside, Iotrolan, Iotroxic Acid, Iotyrosine I 131, Ioversol, Ioxagiate Sodium, Ioxaglate Meglumine, Ioxaglic Acid, ioxilan, Ioxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isoflurophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, Latuda (lurisadone), laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, Leuprolide Acetate, leuprolide+estrogen+progesterone, leuprorelin, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, lodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcainide Hydrochloride, Loreclezole, Loreinadol, lorglumide, Lormetazepam, Lomoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lurasidone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 8708, Martek 92211, Masoprocol, maspin, massetolide, matrilysin inhibitors, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Methynodiol Diacelate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoquizine, metrifonate, Metrizamide, Metrizoate Sodium, Metronidazole, Meturedepa, Metyrapone, Metyrosine, Mexiletine Hydrochloride, Mexrenoate Potassium, Mezlocillin, mfonelic Acid, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecainide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Naldemedine, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxamide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Oformine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, Oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, parthenolide, Partricin, Paulomycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, pentrinitrol, pentrozole, Peplomycin Sulfate, Pepstatin, perflubron, perfofamide, Perfosfamide, pergolide, Perhexiline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenyloin, phosphatase inhibitors, Physostigmine, picenadol, picibanil, Picotrin Diolamine, picroliv, picumeterol, pidotimod, Pifamine, Pilocarpine, pilsicainide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretamide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazo sin, Prazosin Hydrochloride, Prednazate, Prednicarbate, Prednimustine, Prednisolone, Prednisone, Prednival, Pregnenolone Succiniate, Prenalterol Hydrochloride, Pridefine Hydrochloride, Prifelone, Prilocalne Hydrochloride, Prilosec, Primaquine Phosphate, Primidolol, Primidone, Prinivil, Prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurins, Pyrabrom, Pyrantel Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxamide, Ralitoline, raloxifene, raltitrexed, ramatroban, Ramipril, Ramoplanin, ramosetron, ranelic acid, Ranimycin, Ranitidine, ranolazine, Rauwolfia Serpentina, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulon, revaparin sodium, revizinone, rhenium Re 186 etidronate, rhizoxin, Ribaminol, Ribavirin, Riboprine, ribozymes, ricasetron, Ridogrel, Rifabutin, Rifametane, Rifamexil, Rifamide, Rifampin, Rifapentine, Rifaximin, RH retinamide, rilopirox, Riluzole, rimantadine, Rimcazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, rosiglitazone, Rosoxacin, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, R-Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Scrazaipine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofiran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricainide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocainide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcainide, translation inhibitors, traxanox, Trazodone Hydrochloride, Trazodone-HCL, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaninolol, Vapiprost Hydrochloride, Vapreotide, variolin B, Vasopressin, Vecuronium Bromide, velaresol, Velnacrine Maleate, venlafaxine, Veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin, zabicipril, zacopride, zafirlukast, Zalcitabine, zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronie acid, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin.

Another pharmaceutical active acceptable for use herein is lumateperone, as disclosed in U.S. Pat. Nos. 9,745,300, 9,708,322, 7,183,282, 7,071,186, 6,552,017, 8,648,077, 8,598,119, 9,751,883, 9,371,324, 9,315,504, 9,428,506, 8,993,572, 8,309,722, 6,713,471, 8,779,139, 9,168,258, RE039680E1, 9616061, 9586960, and in U.S. Patent Publication Nos. 2017114037, 2017183350, 2015072964, 2004034015, 2017189398, 2016310502, 2015080404, the aforementioned contents of which are incorporated by reference herein in their entirety.

Further examples of antidiabetic actives include but not limited to JTT-501 (PNU-182716) (Reglitazar), AR-H039242, MCC-555 (Netoglitazone), AR-H049020 Tesaglitazar), CS-011 (CI-1037), GW-409544x, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336 and EML-16257.

A wide variety of medicaments, bioactive active substances and pharmaceutical compositions may be included in the dosage forms of the present invention. Examples of useful drugs include ace-inhibitors, anti-anginal drugs, anti-arrhythmia drugs, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremorso preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Controlled Release Dosage Forms

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the dosage forms of the present invention may also be chosen to allow for controlled disintegration of the active. This may be achieved by providing a substantially water insoluble film that incorporates an active that will be released from the dosage form over time. This may be accomplished by incorporating a variety of different soluble or insoluble polymers and may also include biodegradable polymers in combination. Alternatively, coated controlled-release active particles may be incorporated into a readily soluble film matrix to achieve the controlled-release property of the active inside the digestive system upon consumption.

Films that provide a controlled-release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled-release of an active has advantages in addition to those well-known for controlled-release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film or other dosage-form compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

The actives may be taste-masked prior to incorporation into the film composition, as set forth in U.S. Patent Application Publication No. 2007/0281003, titled, "Polymer Based Films and Drug Delivery Systems Made Therefrom," the entire contents of which is incorporated by reference herein. Taste-masking of actives, as disclosed therein, is described herein below.

Particulate Actives Taste-Masking

The active agents employed in the present invention are incorporated into the film compositions of the present invention in a taste-masked or controlled-release form. Taste-masking is useful to avoid unpleasant taste effects, such as bitterness, often associated with the active agents such as pharmaceuticals. In this embodiment, particles of drug may be coated with taste-masking agents, for example polymers, oils, or waxes. Additionally, organoleptic agents, such as, but not limited to sweeteners and/or flavors, may also be employed in such taste-masked compositions, including in the coating layer of the taste masking agent. In alternative embodiments, the particle coatings impart controlled-release, delayed-release, or sustained-release characteristics, delaying the release of active agent from the particle in the mouth or gut of the consumer.

The taste-masked or controlled-release particles may be any useful organoleptic agent, cosmetic agent, pharmaceutical agent, or combinations thereof. Useful organoleptic agents include flavors and sweeteners. Useful cosmetic agents include breath freshening or decongestant agents, such as menthol, including menthol crystals.

Compositions employing particulate active agents incorporated into films with taste-masked coatings are disclosed in PCT application WO 2003/030883, titled "Uniform Films For Rapid Dissolve Dosage Form Incorporating Taste-Masking Compositions," the entire subject matter of which is incorporated by reference herein. As used in this application, any reference to taste-masking by coating particulate active agents should also be understood to encompass controlled-release coatings of particulate active agents.

An important consideration for the film based drug delivery compositions involving a controlled-release or taste-mask particle technology is that the drug containing particles remain chemically stable and do not release the active drug during the mixing and film forming operations of the manufacturing process. Accordingly, with respect to films formed by a wet casting method, the controlled-release or taste-mask particle compositions should be sufficiently stable in the mixer prior to the film forming steps, and the casting and drying steps, so that the particles remain intact in the finished product. In the hot melt extrusion film manufacturing process, the particles must be stable in the extrusion apparatus and any subsequent steps, so that the particles remain intact in the finished product.

In one embodiment, the taste-masking or controlled-release agent is a thin film coating over a particulate bioeffecting agent. Useful coatings in this embodiment include polymeric and non-polymeric materials.

Non-limiting examples of polymers include acrylic polymers, cellulosic polymers or vinyl polymers. Non-limiting examples of non-polymeric materials include crown ethers, fully hydrogenated oils and waxes. Moreover, the taste masking agents may be water soluble, water insoluble or partially water soluble.

For example, the coating material may be carboxymethyl cellulose; methyl cellulose; ethyl cellulose; hydroxyl methyl cellulose; hydroxyethyl cellulose; hydroxypropyl cellulose; hydroxypropylmethyl cellulose; hydroxymethylpropyl cellulose; gum arabic; xanthan gum; tragacanth; acacia; carageenan; guar gum; locust bean gum; pectin; alginates; gelatinized, modified or unmodified starch, including tapioca starch, rice starch, corn starch, potato starch, and wheat starch; polyvinyl alcohol; polyacrylic acid; polyvinyl pyrrolidone; poly(meth)acrylate; poly(meth)copolymers; dextrin; dextran; proteins, such as, gelatin, zein, gluten, soy protein, soy protein isolate, and whey protein; whey protein isolate; casein; levin; collagen; chitin; chitosin; polydextrose and combinations thereof.

Useful acrylic polymers include those available under the trade name Eudragit® from Rohm America, LLC, such as methacrylic acid co-polymers sold under the trade names Eudragit E®, Eudragit L®, Eudragit RD® and Eudragit S®, and polyethylacrylate-methylmethacrylate sold under the trade name, Eudragit NE®. These acrylic polymers are generally water soluble materials.

Useful cellulosic polymers include alkylcelluloses such as methyl or ethyl cellulose, and hydroxyalkylcelluloses, such as hydroxylmethyl cellulose, hydroxyethyl cellulose, hydroxypropyl cellulose, hydroxypropylmethyl cellulose, hydroxymethylpropyl cellulose, and combinations thereof. Useful alkylcelluloses include those sold under the trade names Methocel E™ by Dow Chemicals. Additionally, useful ethylcelluloses are commercially available commercially available from FMC Corporation under brand name Aquacoat ECD. These polymers are generally water soluble materials.

Moreover, the pharmaceutically active agents may be sprayed and congealed with fully hydrogenated oils or waxes considered safe for human consumption and are relatively stable. Useful, but non-limiting, pharmaceutically acceptable oils include mineral oil, peanut oil, soybean oil, sunflower oil, corn oil, olive oil, hard palm oil and rapeseed oil.

Furthermore, crown ether compounds, such as cyclodextrins, are also useful for coating the pharmaceutically active agents. The pharmaceutically active agents are taste masked with crown ethers through entrapment or coaccervation methods. Useful cyclodextrins are commercially available under the trade name of Trappsol® from CTD, Inc.

In some embodiments, the aforementioned polymeric coatings that affect taste masking may be desirable over complexation with ion exchange resins, as has been disclosed in, for example, European Patent No. EP1267829 B1, because of the high drug loadings that are possible with the polymeric coatings as compared to complexation with ion exchange resins. Despite allegations to the contrary, we have found the highest useful drug loading on an ion exchange resin is about 30% by weight. By contrast, the particle coating of this invention can be used with 50-95% drug loading, meaning that a taste-masked particle can contain up to about 95% by weight active and as little as 5% by weight taste-masking polymer. This is a substantially greater drug loading than known ion exchange resins, and very important given the limited size and weight of a film dosage unit, in which maximizing drug loading into a uniform film is an important consideration.

In some embodiments, the taste-masking or control-release agent may be present in the amount of about 5-80% by weight of the particle. In another embodiment, the taste-masking agent is present in the amount of about 5-60% by weight of the particle. In yet another embodiment, the taste-masking agent is present in the amount of about 25-35% by weight of the particle. The precise loading of drug in the taste-mask coated particle is a function of many parameters, including the drug, the coating, and any flavors present in the particle or the film forming matrix.

Pharmaceutically active agents may be taste-masked with the above-described taste-masking agents by a variety of techniques. The techniques coat the pharmaceutically active agents or portions of the pharmaceutically active agents with taste-masking agents to avoid unpleasant taste effects, such as bitterness, often associated with the pharmaceutically active agents or drugs. Useful coating techniques include, but are not limited to, fluidized bed coating, spray congealing coating, agglomeration or granulation coating, entrapment coating, coaccervation coating, infusion coating, spin coating, ion exchange coating and the like.

The fluidized bed coating method is commonly used in pharmaceutical industries for taste masking pharmaceutically active agents. Fluidized bed coaters achieve fluidization of the pharmaceutically active agents by introducing a continuous stream of process gas into a chamber. The coating material is deposited onto the suspended agent as it passes through the spray path of the coating material. The coated agent is dried. A relative low water solubility polymer is typically used to coat the active particles' surface. Minimum limits on particle sizes are about 100 to 120 microns. Smaller particle sizes are difficult to achieve due to process limitation and product loss. Water insoluble pharmaceutically active agents may be suitable coated with water soluble taste masking agents with this method.

In the spray congealing method both the pharmaceutically active agents and the coating materials are sprayed simultaneously into a chamber supplied with process gas to create a uniformly coated active. This method typically involves the coating of the actives with material that could be melted at reasonable temperatures, for example fatty materials or polymers such as certain Eudragit® polymers. The mix of materials are sprayed through a fine nozzle and cooled through a temperature-control air stream or a cold surface. Consideration of mixture temperature is important. The melting temperature of the coating agent selected should not exceed a degradation temperature of the pharmaceutically active agent.

In the agglomeration or granulation method, the pharmaceutically active agents are mixed with the taste-masking agents and a solvent by mechanical means or by spray drying. The solvent is gradually removed by vacuum or heating, or both. Particles are then agglomerated. The agglomerated particles are not typically coated entirely with the taste masking agent and some bitterness may result accordingly. The bitterness, however, may be further reduced by incorporating such coated particles in the films of the present invention.

In typical entrapment coating methods, certain compounds having specific properties that can trap pharmaceutically active agents into its molecule cages must first be selected. Compounds, like certain specifically made starches and crown ether type molecules, such as cyclodextrins and zeolites, are useful with this method. The compounds and the agents are entrapped by ionic attraction. The entrapped agents are then precipitated from solution.

The coaccervation coating method uses two polymers with opposite charges in solution. When the solution is neutralized an insoluble matrix will precipitate from solution and trap the pharmaceutically active agents therein. Examples include interactions of gum arabic and gelatin solutions and interactions of cyclodextrins and protein solutions.

In the infusion method pharmaceutically active agents and flavors or sweeteners are dissolved and infused into a polymer matrix to form a dry powder. In spin coating methods, pharmaceutically active agents are combined with sugars or fats and spun into coated particles. Details of the method are disclosed in U.S. Pat. No. 5,028,632, the contents of which are incorporated herein by reference. In ion exchange coating, ionic bonding of pharmaceutically active agents to ion exchange resins masks the tastes of the agents.

Extrusion and spheronization methods may also be used for taste-masking pharmaceutically active particulates. Ratios of active(s) and polymer(s) (such as, starch, cellulose, gum and/or combinations thereof) are first mixed and thicken by adding a small amount of water. The thickened mixture is then extruded through a single or double nozzle screw. Small spherical particles are formed by a Marumerization® process. Desirable particle sizes are obtained through process control and particulate sieving.

Lyophilization (Freeze-Drying) methods may also be used with the practice of the present invention A combination of polymer(s) (such as, starch, gum, cellulose and/or combinations thereof) with active(s) are mixed and dissolved (or dispersed) in aqueous medium. This mixture is then freeze-dried on a pre-form substrate. Desirable particles sizes can be obtained by process control and product sieving.

In some instances, taste-masking may amount to the addition of two components together, neither of which are particularly pleasing to the taste, but which, due to their chemical makeup, counteract each other or allow for a third substance or more of one of the substances to be added without a concomitant reduction in pleasantness of the taste.

The edible water-soluble delivery system of the present invention further includes one or more members selected from antifoaming agents, plasticizing agents, surfactants, emulsifying agents, thickening agents, binding agents, cooling agents, saliva-stimulating agents, sweetening agents, antimicrobial agents, antigens and combinations thereof.

The particles used in the present invention desirably have a particle size of less than about 200 microns and the taste-masking agent is present in amounts of about 15-80% by weight of the particle. A particle size of about 150 microns or less is also useful. Desirably, the particle size of the particle is about 100 microns or less. Desirably, the thickness of the film is less than about 380 microns, for example, less than about 250 microns. Furthermore, the taste-masking agent may be present in the amount of about 20-60% by weight of the particle. Desirably, the taste-masking agent is present in the amount of about 25-35% by weight of the particle.

In some embodiments, the particulate bioeffecting agent coated with a taste-masking or controlled-release polymer may have a particle size of between 50 to 250 microns. Desirably, the size of the combined particulate and taste-masking agent have a particle size of 150 microns or less, for example 100 microns or less. Particle sizes less than 50 microns may be unsuitable in some embodiments because it is inefficient to coat such small particles due to the large surface area.

Particle sizes of greater than 250 microns may be unsuitable in some embodiments because the larger particles can "bridge" during the film forming process, meaning that the particle can extend from the bottom surface to the top surface of the film, or even protrude beyond the surface of the film. Such bridging may cause streaking and non-uniformity of the finished film. Any protruding particles also may be subject to environmental stresses and premature decomposition, leading to non-uniformity of dosing.

The aforementioned particles may be spherical, substantially spherical, or non-spherical, such as irregularly shaped particles or ellipsoidally shaped particles. Ellipsoidally shaped particles or ellipsoids are especially desirable because of their ability to maintain uniformity in the film forming matrix as they tend to settle to a lesser degree as compared to spherical particles.

When an active agent is present in the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e., a drug.

The uniformity is determined by the presence of no more than a 10% by weight of drug variance throughout the matrix. Desirably, the drug variance is less than 5% by weight, less than 2% by weight, less than 1% by weight, or less than 0.5% by weight. Moreover, the particulates have a particle size of 200 microns or less. Furthermore, the film matrix desirably has a thickness of less than about 380 microns.

Additives

A variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added prior to or along with the active ingredient(s).

Flavors

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Useful flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, and the like may also be used. Further examples of aldehyde flavorings include, but are not limited to acetaldehyde (apple); benzaldehyde (cherry, almond); cinnamicaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape; mixtures thereof; and the like.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The amount of flavoring employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1 to about 30 wt % are useful with the practice of the present invention.

Sweeteners

Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenylglycine, L-aspartyl-2,5-dihydro-L-phenylalanine, L-aspartyl-L-(1-cyclohexyen)-alanine, and the like; water-soluble sweeteners derived from naturally occurring water-soluble sweeteners, such as a chlorinated derivatives of ordinary sugar (sucrose), known, for example, as sucralose; and protein based sweeteners such as *Thaurnatoccous danielli* (Thaurnatin I and II). Naturally occurring high intensity sweeteners, such as Lo Han Kuo, stevia, steviosides, monellin, and glycyrrhizin, may also be used.

In general, an effective amount of auxiliary sweetener is utilized to provide the level of sweetness desired for a particular composition, and this amount will vary with the sweetener selected. This amount will normally be 0.01% to about 10% by weight of the composition. These amounts may be used to achieve a desired level of sweetness independent from the flavor level achieved from any optional flavor oils used. Of course, sweeteners need not be added to films intended for non-oral administration.

Colors

Color additives useful in this invention include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

The illustrations of embodiments of the invention described herein are intended to provide a general understanding of the structure of the various embodiments, and they are not intended to serve as a complete description of all the elements and features of apparatus and systems that might make use of the structures described herein. Many other embodiments will become apparent to those of skill in the art given the teachings herein. Other embodiments are utilized and derived therefrom, such that structural and logical substitutions and changes are made without departing from the scope of this disclosure. Figures are also merely representational and are not necessarily drawn to scale. Certain proportions thereof may be exaggerated, while others diminished in order to facilitate an explanation of the embodiments of the invention. Accordingly, the specification and drawings are to be regarded in an illustrative rather than a restrictive sense.

Such embodiments of the inventive subject matter are referred to herein, individually and/or collectively, by the term "embodiment" merely for convenience and without intending to voluntarily limit the scope of this application to any single embodiment or inventive concept if more than one is in fact shown. Thus, although specific embodiments have been illustrated and described herein, it should be appreciated that any arrangement calculated to achieve the same purpose are substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single embodiment. Thus the following claims are hereby incorporated into the Detailed Description, with each claim standing on its own as a separate example embodiment.

EXPERIMENTAL

Example 1

FIG. 3 is a block diagram of an embodiment of a machine in the form of a computing system 100, within which is a set of instructions 102 that, when executed, cause the machine to perform any one or more of the methodologies according to embodiments of the invention. In some embodiments, the machine operates as a standalone device. In some embodiments, the machine is connected (e.g., via a network 122) to other machines. In a networked implementation, the machine operates in the capacity of a server or a client user machine in a server-client user network environment. Exemplary implementations of the machine as contemplated by the invention include, but are not limited to, a server computer, client user computer, personal computer (PC), tablet PC, Personal Digital Assistant (PDA), cellular telephone, mobile device, palmtop computer, laptop computer, desktop computer, communication device, personal trusted device, web appliance, network router, switch or bridge, or any machine capable of executing a set of instructions (sequential or otherwise) that specify actions to be taken by that machine.

The computing system 100 includes a processing device(s) 104 (e.g., a central processing unit (CPU), a graphics processing unit (GPU), or both), program memory device(s) 106, and data memory device(s) 108, which communicate with each other via a bus 110. The computing system 100 further includes display device(s) 112 (e.g., liquid crystals display (LCD), flat panel, solid-state display, or cathode ray tube (CRT)). The computing system 100 includes input device(s) 116 (e.g., a keyboard), cursor control device(s) 126 (e.g., a mouse), disk drive unit(s) 114, signal generation device(s) 118 (e.g., a speaker or remote control), and network interface device(s) 124, operatively coupled together, and/or with other functional blocks, via bus 110. The disk drive unit(s) 114 includes machine-readable medium(s) 120, on which is stored one or more sets of instructions 102 (e.g., software) embodying any one or more of the methodologies or functions herein, including those methods illustrated herein. The instructions 102 also reside, completely or at least partially, within the program memory device(s) 106, the data memory device(s) 108, and/or the processing device(s) 104 during execution thereof by the computing system 100. The program memory device(s) 106 and the processing device(s) 104 also constitute machine-readable media. Dedicated hardware implementations, such as but not limited to application specific integrated circuits, programmable logic arrays, and other hardware devices can likewise be constructed to implement the methods described herein. Applications that include the apparatus and systems of various embodiments broadly comprise a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments, the methods, functions or logic described herein is implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

The embodiment contemplates a machine-readable medium or computer-readable medium containing instructions 102, or that which receives and executes instructions 102 from a propagated signal so that a device connected to a network environment 122 can send or receive voice, video or data, and to communicate over the network 122 using the instructions 102. The instructions 102 are further transmitted or received over the network 122 via the network interface device(s) 124. The machine-readable medium also contains a data structure for storing data useful in providing a functional relationship between the data and a machine or computer in an illustrative embodiment of the systems and methods herein.

While the machine-readable medium 120 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform anyone or more of the methodologies of the embodiment. The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and/or a digital file attachment to e-mail or other self-contained information archive or set of archives is considered a distribution medium equivalent to a tangible storage medium. Accordingly, the embodiment is considered to include anyone or more of a tangible machine-readable medium or a tangible distribution medium, as listed herein and including art-recognized equivalents and successor media, in which the software implementations herein are stored.

It should also be noted that software, which implements the methods, functions or logic herein, are optionally stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

As previously stated, although the specification describes components and functions implemented in accordance with embodiments of the invention with reference to particular standards and protocols, the embodiments are not limited to such standards and protocols.

The Abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single embodiment. Thus the following claims are hereby incorporated into the Detailed Description, with each claim standing on its own as separately claimed subject matter.

Although specific example embodiments have been described, it will be evident that various modifications and changes are made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and without limitation, specific embodiments in which the subject matter are practiced. The embodiments illustrated are described in sufficient detail to enable those skilled in the art to practice the teachings herein. Other embodiments are utilized and derived therefrom, such that structural and logical substitutions and changes are made without departing from the scope of this disclosure. This Detailed Description, therefore, is not to be taken in a limiting sense, and the scope of various embodiments is defined only by the appended claims, along with the full range of equivalents to which such claims are entitled.

Given the teachings of the invention provided herein, one of ordinary skill in the art will be able to contemplate other implementations and applications of the techniques of the invention. Although illustrative embodiments of the invention have been described herein with reference to the accompanying drawings, it is to be understood that the invention is not limited to those precise embodiments, and that various other changes and modifications are made therein by one skilled in the art without departing from the scope of the appended claims.

What is claimed:

1. A system to create one or more personalized individual unit doses associated with treatment of an individual, the system comprising:
a polymer carrier matrix selected from the group consisting of polyethylene oxide, polyvinyl pyrrolidone, polyvinyl alcohol, hydrophilic cellulosic polymer, and combinations thereof;
an active;
an apparatus configured to combine the polymer carrier matrix and the active into a self-supporting film using a mixing and film-forming process which provides for uniformity of content in IUD's cut from said film the apparatus being a film-forming assembly or a sheet-forming assembly selected from the group consisting of a wet casting assembly or a hot melt extrusion assembly, and optionally further including a spray-drying assembly;
a networked control system comprising:
computing device; and
a memory storage storing executable instructions that, when executed by the computing device, cause the computing device to perform operations comprising:
electronically communicating health information measured from the individual to a medical professional who determines a medical prescription based on the health information, the medical prescription comprising a prescribed amount of the active to be included in the personalized individual unit dose (IUD);
electronically communicating the medical prescription from the medial professional to an IUD manufacturer and directing the IUD manufacturer to make the film from the polymer carrier matrix and the active using the apparatus in accordance with the prescribed amount of the active comprised in the medical prescription associated with treatment of the individual; and
an additional apparatus for dividing or cutting the self-supporting film into a plurality of personalized IUDs, wherein each of the personalized IUDs contain an amount of the active which does not vary more than 10% from the prescribed amount of the active.

2. The system of claim 1, wherein the networked system further includes at least one of a display device, an alpha-numeric input device, a cursor control device, a drive unit, a machine-readable medium, and a signal generation device.

3. The system of claim 1, comprising a biometric measurement module that interfaces with the individual.

4. The system of claim 3, wherein the biometric measurement module comprises at least one measurement device selected from a group consisting of invasive, and non-invasive measurement devices, and combinations thereof.

5. The system of claim 3, wherein the biometric measurement module comprises a device selected from the group consisting of acoustical instruments, visual instruments, tactile instruments, chemical instruments, biological instruments, electrical instruments, thermal instruments and combinations thereof.

6. The system of claim 3, wherein the biometric measurement module comprises a device selected from the group consisting of cameras, video scopes, illumination systems, colorimeters, spirometers, holter monitors, vital sign monitors, signal monitors, sensors, ultrasound probes, machines which measure electric signals from the body, blood chemistry instruments, blood flow measurement devices, blood content measurement devices, thermal measurement devices and combinations thereof.

7. The system of claim 3, wherein the biometric measurement module comprises a device selected from the group consisting of electroencephalogram (EEG) machines, electrocardiogram (EKG) machines, electromyogram (EMG) machines, echocardiogram (ECG) machines, atrial fibrillation devices, stethoscopes, pharyngoscopes, sinus scopes, otoscopes, laparoscopes, dermascopes, blood gas measurement devices, multi-purpose cameras, retinal cameras, ocular measurement devices, intraoral cameras, abdominal ultrasound devices, vascular ultrasound devices, trans-vaginal ultrasound devices, skin surface measurement devices which measure one or more of temperature, blood flow, blood sugar, skin color, skin texture, blood-fat content, blood cholesterol content, accelerometers, movement sensors, and combinations thereof.

8. The system of claim 3, wherein the biometric measurement module is a least one device comprising one or more software applications which are used to obtain the biometric information, information which is used in making a diagnosis, information used in the medical evaluation, information used in evaluating the treatment effectiveness and/or change in treatment necessary for the individual, or a combination thereof.

9. The system of claim 8, wherein the least one device is selected from the group consisting of an implant, computer, phone, mobile phone, computer tablet, computer laptop, watch, wearable device and combinations thereof.

10. The system of claim 1, wherein the medical prescription further includes a formulation for the carrier matrix.

11. The system of claim 1, wherein the hydrophilic cellulosic polymer is polymer carrier matrix comprises a polymer selected from the group consisting of hydroxypropylmethyl cellulose, hydroxypropyl cellulose, and combinations thereof.

12. The system of claim 10, wherein the pharmaceutical formulation includes a solvent selected from the group consisting of water, alcohol, acetone, methylene chloride and combinations thereof.

13. The system of claim 10, wherein the pharmaceutical formulation includes a component selected from the group consisting of adjuvants, permeation enhancers, plasticizers, thickeners, rheological modifiers, solvents, alcohols, extenders, colorants, pigments, sweeteners, flavors and combinations thereof.

14. The system of claim 1, wherein the active is selected from the group comprising a pharmaceutical active, small molecules, macromolecules, biologics, microorganisms, allergens, enzymes, and combinations thereof.

15. The system of claim 1, wherein the active is a pharmaceutical or bioactive substance selected from the group consisting of ace-inhibitors, anti-anginal drugs, anti-arrhythmia drugs, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremorso preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

16. The system of claim 1, wherein the medical prescription includes a pharmaceutical active, a bioactive, prodrug, derivative, analogue or a combination thereof.

17. The system of claim 16, wherein the pharmaceutical active or bioactive is selected from the group consisting of a prescription active, an OTC active, a homeopathic active, and a combination thereof.

18. The system of claim 1, further including a database or network system for storing the health information in a database or network system.

19. The system of claim 1, further comprising a blending (mixing) assembly, a compounding assembly, a packaging assembly, a labeling assembly, an embossing assembly, a scoring assembly, and combinations thereof.

20. The system of claim 19, further comprising a quality control assembly.

* * * * *